United States Patent
Weier et al.

[11] Patent Number: 5,916,905
[45] Date of Patent: Jun. 29, 1999

[54] 2,3-SUBSTITUTED PYRIDINES FOR THE TREATMENT OF INFLAMMATION

[75] Inventors: Richard M Weier, Lake Bluff, Ill.; Len F Lee, St. Charles, Mo.; Richard A Partis, Evanston; Francis J Koszyk, Prospect Heights, both of Ill.

[73] Assignee: G. D. Searle & Co., Skokie, Ill.

[21] Appl. No.: 08/894,102

[22] PCT Filed: Feb. 8, 1996

[86] PCT No.: PCT/US96/01111

§ 371 Date: Aug. 8, 1997

§ 102(e) Date: Aug. 8, 1997

[87] PCT Pub. No.: WO96/24584

PCT Pub. Date: Aug. 15, 1996

Related U.S. Application Data

[63] Continuation-in-part of application No. 08/387,150, Feb. 10, 1995.

[51] Int. Cl.6 .................................................. A61K 31/44
[52] U.S. Cl. ...................... 514/345; 514/277; 514/344; 514/352; 514/355; 546/286; 546/290; 546/291; 546/304
[58] Field of Search ..................... 514/344, 345, 514/346, 349, 277, 352, 355; 546/286, 290, 291, 304

[56] References Cited
FOREIGN PATENT DOCUMENTS 1238959   7/1971   United Kingdom .

Primary Examiner—Amelia Owens
Attorney, Agent, or Firm—Joseph W. Bulock; Scott Williams

[57] ABSTRACT

A class of substituted pyridyl compounds is described for use in treating inflammation and inflammation-related disorders. Compounds of particular interest are defined by Formula II (II)

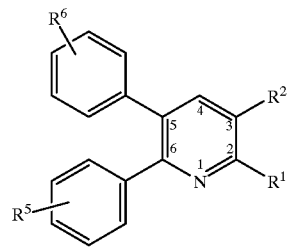

wherein $R^1$ is selected from hydrido, halo, alkoxy, haloalkoxy, aryl, alkylthio, alkylamino, aralkoxy, azido and alkenyloxy; wherein $R^2$ is selected from hydrido, cyano, hydroxyalkyl, haloalkyl, aminoalkyl, alkylaminoalkyl, alkylcarbonyloxyalkyl, aminocarbonyl and alkylcarbonylaminoalkyl; and wherein $R^5$ and $R^6$ are one or more radicals independently selected from halo, alkylsulfonyl, aminosulfonyl, alkoxy and alkylthio; provided one of $R^5$ and $R^6$ is substituted with alkylsulfonyl, aminosulfonyl, or haloalkylsulfonyl; or a pharmaceutically-acceptable salt thereof.

29 Claims, No Drawings

2,3-SUBSTITUTED PYRIDINES FOR THE TREATMENT OF INFLAMMATION

REFERENCE TO RELATED APPLICATIONS

This application is a continuation-in-part application of U.S. application Ser. No. 08/387,150, filed Feb. 10, 1995. This application is also a 35 U.S.A. §371 national stage application based on PCT application Ser. No. PCT/US96/01111 filed Feb. 8, 1996.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel pyridines disclosed herein are such safe and also effective antiinflammatory agents furthering such efforts. The invention's compounds are found to show usefulness i vivo as antiinflammatory agents with minimal side effects. The substituted pyridinyl compounds disclosed herein preferably selectively inhibit cyclooxygenase-2 over cyclooxygenase-1.

Pyridines have been described for various uses, including the treatment of inflammation. U.S. Pat. No. 5,225,418 to Miller, describes 4-(1H)-quinolinones as intermediates in the preparation of antiinflammatory agents.

European Application, EP388,619, published Sep. 26, 1990, describes a method of preparing pyridine-2,3-dicarboxylic acids.

European Application, EP308,020, published Mar. 22, 1989, describes 1,2-dihydro-2-oxo-3-pyridylcarboxylic acids as having antibiotic activity. 5-(4-Fluorophenyl)-1,2-dihydro-6-[4-(methylsulfonyl)phenyl]-2-oxo-pyridyl-3-carboxylic acid is specifically described.

U.S. Pat. No. 3,655,679, to Shen et al, describes aryl pyridine carboxylic acids as having antiinflammatory activity.

British Pat. No. 1,238,959 describes pyridyl derivatives as having antiinflammatory activity. Specifically, 4-(2-1H-pyridon-3-yl)benzenesulfonamide is described.

U.S. Pat. No. 4,011,328, to Pinhas et al, describes derivatives of pyridine-3-acetic acid as having antiinflammatory properties. Specifically, [5-(4-fluorophenyl)-6-[4-(methylthio)phenyl]-2-methyl-3-pyridyl]acetic acid is described. U.S. Pat. No. 4,533,666, to Matsumoto et al, describes 6-phenyl-2,3-(4-methoxyphenyl)pyridine derivatives as having antiinflammatory properties.

The invention's pyridyl compounds are found to show usefulness in vivo as antiinflammatory agents with minimal side effects.

DESCRIPTION OF THE INVENTION

A class of substituted pyridyl compounds useful in treating inflammation-related disorders is defined by Formula I:

(I)

wherein $R^1$ is selected from hydrido, halo, alkyl, haloalkyl, alkoxy, haloalkoxy, aryl, alkylthio, alkylamino, aralkoxy, aralkylthio, aralkylamino, N-alkyl-N-aralkylamino, heteroaralkoxy, heteroaralkylthio, heteroaralkylamino, N-alkyl-N-heteroaralkylamino, cycloalkylalkoxy, cycloalkyialkylthio, N-alkyl-N-cycloalkylalkylamino, azido, arylcarbonylalkoxy, arylcarbonylthio, alkoxycarbonylalkoxy, alkylaminocarbonylalkoxy, alkoxycarbonylalkylthio, alkylaminocarbonylalkylthio, arylcarbonylalkylamino, alkoxycarbonylalkylamino, alkenylthio, alkenylamino, N-alkyl-N-alkenylamino, arylalkenyloxy and alkenyloxy;

wherein $R^2$ is selected from hydrido, cyano, hydroxyalkyl, haloalkyl, aminoalkyl, alkoxyalkyl, aralkoxyalkyl, alkylthioalkyl, aralkylthioalkyl, alkylaminoalkyl, aryloxyalkyl, arylthioalkyl, alkylcarbonyloxyalkyl, aminocarbonyl and alkylcarbonylaminoalkyl; and wherein $R^3$ and $R^4$ are independently selected from aryl and heteroaryl, wherein $R^3$ and $R^4$ are optionally substituted at a substitutable position with one or more radicals independently selected from hydrido, alkyl, cyano, carboxyl, alkoxycarbonyl, haloalkyl, hydroxyl, hydroxyalkyl, haloalkoxy, amino, alkylamino, arylamino, nitro, alkoxyalkyl, alkylsulfinyl, halo, alkylsulfonyl, aminosulfonyl, haloalkylsulfonyl, alkoxy and alkylthio;

provided one of $R^3$ and $R^4$ is phenyl substituted with alkylsulfonyl, aminosulfonyl, or haloalkylsulfonyl;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis. Such compounds of the invention would be useful in the treatment of asthma, bronchitis, menstrual cramps, tendinitis, bursitis, and skin-related conditions such as psoriasis, eczema, burns and dermatitis. Compounds of the invention also would be useful to treat gastrointestinal conditions such as inflammatory bowel disease, Crohn's disease, gastritis, irritable bowel syndrome and ulcerative colitis, and for the prevention or treatment of cancer, such as colorectal cancer. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases such as retinitis, retinopathies, uveitis, conjunctivitis, and of acute injury to the eye tissue. The compounds would also be useful in the treatment of pulmonary inflammation, such as that associated with viral infections and cystic fibrosis. The compounds would also be useful for the treatment of certain central nervous system disorders such as cortical dementias including Alzheimers disease. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma.

Besides being useful for human treatment, these compounds are also useful for veterinary treatment of mammals, including companion animals and farm animals, such as, but not limited to, horses, dogs, cats, cows, sheep and pigs.

The present compounds may also be used in co-therapies, partially or completely, in place of other conventional antiinflammatories, such as together with steroids, NSAIDs, 5-lipoxygenase inhibitors, $LTB_4$ receptor antagonists and $LTA_4$ hydrolase inhibitors.

Suitable $LTB_4$ receptor antagonists include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the $LTB_4$ receptor antagonists are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present invention preferably includes compounds which selectively inhibit cyclooxygenase-2 over cyclooxygenase-1. Preferably, the compounds have a cyclooxygenase-2 $IC_{50}$ of less than about 0.5 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 IC50 of greater than about 1 $\mu$M, and more preferably of greater than 20 $\mu$M. Such preferred selectivity may indicate an ability to reduce the incidence of common NSAID-induced side effects.

A preferred class of compounds consists of those compounds of Formula I wherein $R^1$ is selected from hydrido, halo, lower alkyl, lower haloalkyl, lower alkoxy, lower haloalkoxy, aryl selected from phenyl, naphthyl and biphenyl, lower alkylthio, lower alkylamino, lower dialkylamino, lower aralkoxy, lower aralkylthio, lower aralkylamino, lower N-alkyl-N-aralkylamino, lower heteroaralkoxy, lower heteroaralkylthio, lower heteroaralkylamino, lower N-alkyl-N-heteroaralkylamino, lower cycloalkylalkoxy, lower cycloalkylalkylthio, lower N-alkyl-N-cycloalkylalkylamino, azido, lower arylcarbonylalkoxy, phenylcarbonylthio, lower alkoxycarbonylalkoxy, lower alkylaminocarbonylalkoxy, lower alkoxycarbonylalkylthio, lower alkylaminocarbonylalkylthio, lower arylcarbonylalkylamino, lower alkoxycarbonylalkylamino, lower alkenylthio, lower alkenylamino, lower N-alkyl-N-alkenylamino, lower arylalkenyloxy and lower alkenyloxy; wherein $R^2$ is selected from hydrido, cyano, lower hydroxyalkyl, lower haloalkyl, lower aminoalkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower alkylcarbonyloxyalkyl, aminocarbonyl and lower alkylcarbonylaminoalkyl; and wherein $R^3$ and $R^4$ are independently selected from phenyl, naphthyl, biphenyl and five to ten membered heteroaryl, wherein $R^3$ and $R^4$ are optionally substituted at a substitutable position with one or more radicals independently selected from hydrido, lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower alkoxyalkyl, nitro, halo, lower alkylsulfonyl, aminosulfonyl, lower alkoxy and lower alkylthio; or a pharmaceutically-acceptable salt thereof.

A more preferred class of compounds consists of those compounds of Formula I wherein $R^1$ is selected from hydrido, halo, lower alkoxy, lower haloalkoxy, lower alkyl aryl selected from phenyl, naphthyl and biphenyl, lower alkylthio, lower N-alkylamino, lower dialkylamino, lower aralkoxy, lower aralkylthio, lower aralkylamino, lower N-alkyl-N-aralkylamino, lower cycloalkylalkoxy, lower cycloalkylalkylthio, lower N-alkyl-N-cycloalkylalkylamino, azido, lower alkenylthio and lower alkenyloxy; wherein $R^2$ is selected from hydrido, cyano, lower hydroxyalkyl, lower haloalkyl, lower aminoalkyl, lower alkylaminoalkyl, lower alkylcarbonyloxyalkyl, aminocarbonyl and lower alkylcarbonylaminoalkyl; and wherein $R^3$ and $R^4$ are independently selected from phenyl, naphthyl, biphenyl, and five or six membered heteroaryl, wherein $R^3$ and $R^4$ are optionally substituted at a substitutable position with one or more radicals independently selected from hydrido, lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, nitro, halo, lower alkylsulfonyl, aminosulfonyl, lower alkoxy and lower alkylthio; or a pharmaceutically-acceptable salt thereof.

An even more preferred class of compounds consists of those compounds of Formula I wherein $R^1$ is selected from hydrido, halo, lower alkyl, lower alkoxy, lower haloalkoxy, phenyl, naphthyl, biphenyl, lower alkylthio, lower N-alkylamino, lower dialkylamino, lower aralkoxy, lower aralkylthio, azido and lower alkenyloxy; wherein $R^2$ is selected from hydrido, cyano, lower hydroxyalkyl, lower haloalkyl, lower aminoalkyl, lower alkylaminoalkyl, lower alkylcarbonyloxyalkyl, aminocarbonyl and lower alkylcarbonylaminoalkyl; and wherein $R^3$ and $R^4$ are independently selected from phenyl, pyridyl, and thienyl, wherein $R^3$ and $R^4$ are optionally substituted at a substitutable position with one or more radicals independently selected from hydrido, lower alkyl, lower haloalkyl, lower haloalkoxy, amino, lower alkylamino, halo, lower alkylsulfonyl, aminosulfonyl, lower alkoxy and lower alkylthio; or a pharmaceutically-acceptable salt thereof.

A class of compounds of particular interest consists of those compounds of Formula I wherein $R^1$ is selected from hydrido, fluoro, chloro, bromo, methyl, methoxy, ethoxy, propoxy, n-butoxy, pentoxy, hexyloxy, trifluoromethoxy, 4,4,4-trifluorobutoxy, 3,3,3-trifluoropropoxy, phenyl, naphthyl, biphenyl, methylthio, ethylthio, butylthio, hexylthio, methylamino, ethylamino, dimethylamino, butylamino, benzyloxy, phenylethoxy, 4-chlorophenoxy, naphthylmethoxy, benzylthio, phenylethylthio, naphthylmethylthio, azido, and alkenyloxy; wherein $R^2$ is selected from hydrido, cyano, hydroxymethyl, 1-methylmethanol, trifluoromethyl, difluoromethyl, fluoromethyl, aminomethyl, N,N-dimethylaminomethyl, N-methylaminomethyl, methylcarbonyloxymethyl, propylcarbonyloxymethyl, propylcarbonyloxyethyl, tert-butylcarbonyloxymethyl, aminocarbonyl and methylcarbonylaminomethyl; and wherein $R^3$ and $R^4$ are independently selected from phenyl, 2-pyridyl, 3-pyridyl and 4-pyridyl, wherein $R^3$ and $R^4$ are optionally substituted at a substitutable position with one or more radicals independently selected from hydrido, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, trifluoromethoxy, amino, N-methylamino, N,N-dimethylamino, N-ethylamino, N,N-dipropylamino, N-butylamino, N-methyl-N-ethylamino, fluoro, chloro, bromo, methylsulfonyl, aminosulfonyl, methoxy, methylenedioxy, ethoxy, propoxy, n-butoxy, ethylthio, butylthio, hexylthio and methylthio; or a pharmaceutically-acceptable salt thereof.

A family of specific compounds of particular interest within Formula I consists of compounds and pharmaceutically-acceptable salts thereof as follows:

2-butoxy-6-(4-fluorophenyl)-N,N-dimethyl-5-[4-(methylsulfonyl)phenyl]pyridine-3-methanamine;
2-butoxy-6-(4-fluorophenyl)-5-[4-(methylsulfonyl)phenyl]pyridine-3-methanol, acetate;
[2-butoxy-6-(4-fluorophenyl)-5-[4-(methylsulfonyl)phenyl]pyridin-3-yl]methylbutanoate;
[2-butoxy-6-(4-fluorophenyl)-5-[4-(methylsulfonyl)phenyl]pyridin-3-yl]methyl-2,2-propanoate;
2-butoxy-6-(4-fluorophenyl)-N-methyl-5-[4-(methylsulfonyl)phenyl]pyridine-3-methanamine;
(+/−) 2-butoxy-6-(4-fluorophenyl)-α-methyl-5-[4-(methylsulfonyl)phenyl]pyridine-3-methanol;
(+/−) 1-[2-butoxy-6-(4-fluorophenyl)-5-[4-(methylsulfonyl)phenyl]pyridin-3-yl]ethylbutanoate;
5-[4-(aminosulfonyl)phenyl]-2-butoxy-6-(4-fluorophenyl)-N,N-dimethyl-pyridine-3-methanamine;
5-[4-(aminosulfonyl)phenyl]-2-butoxy-6-(4-fluorophenyl)-pyridine-3-methanol, acetate;
[5-[4-(aminosulfonyl)phenyl]-2-butoxy-6-(4-fluorophenyl)-pyridin-3-yl]methylbutanoate;
[5-[4-(aminosulfonyl)phenyl]-2-butoxy-6-(4-fluorophenyl)-pyridin-3-yl]methyl-2,2-propanoate;
5-[4-(aminosulfonyl)phenyl]-2-butoxy-6-(4-fluorophenyl)-N-methyl-pyridine-3-methanamine;
(+/−) 5-[4-(aminosulfonyl)phenyl]-2-butoxy-6-(4-fluorophenyl)-α-methyl-pyridine-3-methanol;
(+/−) 1-[5-[4-(aminosulfonyl)phenyl]-2-butoxy-6-(4-fluorophenyl)-pyridin-3-yl]ethylbutanoate;
2-butoxy-6-(4-methylphenyl)-5-[4-(methylsulfonyl)phenyl]pyridine-3-carbonitrile;
2-butoxy-6-(3-methylphenyl)-5-[4-(methylsulfonyl)phenyl]pyridine-3-carbonitrile;
2-butoxy-6-(3-methoxyphenyl)-5-[4-(methylsulfonyl)phenyl]pyridine-3-carbonitrile;
2-butoxy-5-[4-(methylsulfonyl)phenyl]-6-(4-methylthiophenyl)pyridine-3-carbonitrile;
2-butoxy-5-[4-(methylsulfonyl)phenyl]-6-(3-methylthiophenyl)pyridine-3-carbonitrile;
6-(4-bromophenyl)-2-butoxy-5-[4-(methylsulfonyl)phenyl]pyridine-3-carbonitrile;
2-butoxy-6-(4-chlorophenyl)-5-[4-(methylsulfonyl)phenyl]pyridine-3-carbonitrile;
2-butoxy-6-(3-chloro-4-methoxyphenyl)-5-[4-(methylsulfonyl)phenyl]pyridine-3-carbonitrile;
2-butoxy-6-(3-fluoro-4-methoxyphenyl)-5-[4-(methylsulfonyl)phenyl]pyridine-3-carbonitrile;
6-(3-chloro-4-methoxyphenyl)-2-methoxy-5-[4-(methylsulfonyl)phenyl]pyridine-3-methanol;
6-(3-fluoro-4-methoxyphenyl)-2-methoxy-5-[4-(methylsulfonyl)phenyl]pyridine-3-methanol;
6-(3,5-difluoro-4-methoxyphenyl)-2-methoxy-5-[4-(methylsulfonyl)phenyl]pyridine-3-methanol;
2-butoxy-6-(4-methylphenyl)-5-[4-(methylsulfonyl)phenyl]pyridine-3-methanol;
2-butoxy-6-(3-methylphenyl)-5-[4-(methylsulfonyl)phenyl]pyridine-3-methanol;
2-butoxy-6-(3-methoxyphenyl)-5-[4-(methylsulfonyl)phenyl]pyridine-3-methanol;
2-butoxy-5-[4-(methylsulfonyl)phenyl]-6-(4-methylthiophenyl)pyridine-3-methanol;
2-butoxy-5-[4-(methylsulfonyl)phenyl]-6-(3-methylthiophenyl)pyridine-3-methanol;
2-butoxy-6-(4-chlorophenyl)-5-[4-(methylsulfonyl)phenyl]pyridine-3-methanol;
2-butoxy-6-(3-chloro-4-methoxyphenyl)-5-[4-(methylsulfonyl)phenyl]pyridine-3-methanol;
2-butoxy-6-(3-fluoro-4-methoxyphenyl)-5-[4-(methylsulfonyl)phenyl]pyridine-3-methanol;
2-fluoro-6-(4-fluorophenyl)-5-[4-(methylsulfonyl)phenyl]pyridine-3-carbonitrile;
2-bromo-6-(4-fluorophenyl)-5-[4-(methylsulfonyl)phenyl]pyridine-3-carbonitrile;
2-ethoxy-6-(4-fluorophenyl)-5-[4-(methylsulfonyl)phenyl]pyridine-3-carbonitrile;
2-(4-chlorobenzyloxy)-6-(4-fluorophenyl)-5-[4-(methylsulfonyl)phenyl]pyridine-3-carbonitrile;
6-(4-fluorophenyl)-2-(4-fluorobenzyloxy)-5-[4-(methylsulfonyl)phenyl]pyridine-3-carbonitrile;
6-(4-fluorophenyl)-2-(4-methoxybenzyloxy)-5-[4-(methylsulfonyl)phenyl]pyridine-3-carbonitrile;
6-(4-fluorophenyl)-5-[4-(methylsulfonyl)phenyl]-2-(2-quinolylmethoxy)pyridine-3-carbonitrile;
6-(4-fluorophenyl)-5-[4-(methylsulfonyl)phenyl]-2-(4-pyridylmethoxy)pyridine-3-carbonitrile;
6-(4-fluorophenyl)-5-[4-(methylsulfonyl)phenyl]-2-(2-thienylmethoxy)pyridine-3-carbonitrile;
6-(4-fluorophenyl)-2-(2-furylmethoxy)-5-[4-(methylsulfonyl)phenyl]pyridine-3-carbonitrile;

6-(4-fluorophenyl)-5-[4-(methylsulfonyl)phenyl]-2-(phenylethoxy)pyridine-3-carbonitrile;

2-(allyloxy)-6-(4-fluorophenyl)-5-[4-(methylsulfonyl)phenyl]pyridine-3-carbonitrile;

2-(cyclohexylmethoxy)-6-(4-fluorophenyl)-5-[4-(methylsulfonyl)phenyl]pyridine-3-carbonitrile;

2-(cyclopropylmethoxy)-6-(4-fluorophenyl)-5-[4-(methylsulfonyl)phenyl]pyridine-3-carbonitrile;

2-(cyclobutylmethoxy)-6-(4-fluorophenyl)-5-[4-(methylsulfonyl)phenyl]pyridine-3-carbonitrile;

2-(cyclopentylmethoxy)-6-(4-fluorophenyl)-5-[4-(methylsulfonyl)phenyl]pyridine-3-carbonitrile;

6-(4-fluorophenyl)-2-(3-methyl-2-butenyloxy)-5-[4-(methylsulfonyl)phenyl]pyridine-3-carbonitrile;

6-(4-fluorophenyl)-5-[4-(methylsulfonyl)phenyl]-2-(phenylcarbonylmethoxy)pyridine-3-carbonitrile;

6-(4-fluorophenyl)-2-(methoxycarbonylmethoxy)-5-[4-(methylsulfonyl)phenyl]pyridine-3-carbonitrile;

2-(butoxycarbonylmethoxy)-6-(4-fluorophenyl)-5-[4-(methylsulfonyl)phenyl]pyridine-3-carbonitrile;

2-(N,N-dimethylaminocarbonylmethoxy)-6-(4-fluorophenyl)-5-[4-(methylsulfonyl)phenyl]pyridine-3-carbonitrile;

2-(3-chlorobenzylthio)-6-(4-fluorophenyl)-5-[4-(methylsulfonyl)phenyl]pyridine-3-carbonitrile;

2-(4-fluorobenzylthio)-6-(4-fluorophenyl)-5-[4-(methylsulfonyl)phenyl]pyridine-3-carbonitrile;

6-(4-fluorophenyl)-2-(4-methoxybenzylthio)-5-[4-(methylsulfonyl)phenyl]pyridine-3-carbonitrile;

6-(4-fluorophenyl)-5-[4-(methylsulfonyl)phenyl]-2-(2-quinolylmethylthio)pyridine-3-carbonitrile;

6-(4-fluorophenyl)-5-[4-(methylsulfonyl)phenyl]-2-(3-pyridylmethylthio)pyridine-3-carbonitrile;

6-(4-fluorophenyl)-5-[4-(methylsulfonyl)phenyl]-2-(2-thienylmethylthio)pyridine-3-carbonitrile;

6-(4-fluorophenyl)-5-[4-(methylsulfonyl)phenyl]-2-(phenylethylthio)pyridine-3-carbonitrile;

2-(allylthio)-6-(4-fluorophenyl)-5-[4-(methylsulfonyl)phenyl]pyridine-3-carbonitrile;

2-(cyclohexylmethylthio)-6-(4-fluorophenyl)-5-[4-(methylsulfonyl)phenyl]pyridine-3-carbonitrile;

2-(cyclopentylmethylthio)-6-(4-fluorophenyl)-5-[4-(methylsulfonyl)phenyl]pyridine-3-carbonitrile;

6-(4-fluorophenyl)-5-[4-(methylsulfonyl)phenyl]-2-(phenylcarbonylmethylthio)pyridine-3-carbonitrile;

2-(ethoxycarbonylmethylthio)-6-(4-fluorophenyl)-5-[4-(methylsulfonyl)phenyl]pyridine-3-carbonitrile;

2-[N-(4-chlorobenzyl)amino]-6-(4-fluorophenyl)-5-[4-(methylsulfonyl)phenyl]pyridine-3-carbonitrile;

2-[N-(2-fluorobenzyl)amino]-6-(4-fluorophenyl)-5-[4-(methylsulfonyl)phenyl]pyridine-3-carbonitrile;

6-(4-fluorophenyl)-2-[N-(3-methoxybenzyl)amino]-5-[4-(methylsulfonyl)phenyl]pyridine-3-carbonitrile;

6-(4-fluorophenyl)-5-[4-(methylsulfonyl)phenyl]-2-[N-(4-pyridylmethyl)amino]pyridine-3-carbonitrile;

6-(4-fluorophenyl)-5-[4-(methylsulfonyl)phenyl]-2-[N-(3-thienylmethyl)amino]pyridine-3-carbonitrile;

6-(4-fluorophenyl)-2-[N-(2-furylmethyl)amino]-5-[4-(methylsulfonyl)phenyl]pyridine-3-carbonitrile;

6-(4-fluorophenyl)-5-[4-(methylsulfonyl)phenyl]-2-[N-(phenylethyl)amino]pyridine-3-carbonitrile;

2-[N-(allyl)amino]-6-(4-fluorophenyl)-5-[4-(methylsulfonyl)phenyl]pyridine-3-carbonitrile;

2-[N-(cyclohexylmethyl)amino]-6-(4-fluorophenyl)-5-[4-(methylsulfonyl)phenyl]pyridine-3-carbonitrile;

6-(4-fluorophenyl)-5-[4-(methylsulfonyl)phenyl]-2-[N-(phenylcarbonylmethyl)amino]pyridine-3-carbonitrile;

2-(N-ethoxycarbonylmethyl)amino-6-(4-fluorophenyl)-5-[4-(methylsulfonyl)phenyl]pyridine-3-carbonitrile;

4-[6-butoxy-5-cyano-2-(4-methylphenyl)-3-pyridyl]benzensulfonamide;

4-[6-butoxy-5-cyano-2-(3-methylphenyl)-3-pyridyl]benzensulfonamide;

4-[6-butoxy-5-cyano-2-(3-methoxyphenyl)-3-pyridyl]benzensulfonamide;

4-[6-butoxy-5-cyano-2-(4-methylthiophenyl)-3-pyridyl]benzensulfonamide;

4-[6-butoxy-5-cyano-2-(3-methylthiophenyl)-3-pyridyl]benzensulfonamide;

4-[6-butoxy-2-(3-chloro-4-methoxyphenyl)-5-cyano-3-pyridyl]benzensulfonamide;

4-[6-butoxy-5-cyano-2-(3-fluoro-4-methoxyphenyl)-3-pyridyl]benzensulfonamide;

4-[2-(3-chloro-4-methoxyphenyl)-6-methoxy-3-pyridyl]benzensulfonamide;

4-[2-(3-fluoro-4-methoxyphenyl)-6-methoxy-3-pyridyl]benzensulfonamide;

4-[2-(3,5-difluoro-4-methoxyphenyl)-6-methoxy-3-pyridyl]benzensulfonamide;

4-[6-butoxy-2-(3-chloro-4-methoxyphenyl)-3-pyridyl]benzensulfonamide;

4-[6-butoxy-2-(3-fluoro-4-methoxyphenyl)-3-pyridyl]benzensulfonamide;

5-[4-(aminosulfonyl)phenyl]-6-(3-chloro-5-methoxyphenyl)-2-methoxypyridine-3-methanol;

5-[4-(aminosulfonyl)phenyl]-6-(3-fluoro-5-methoxyphenyl)-2-methoxypyridine-3-methanol;

5-[4-(aminosulfonyl)phenyl]-6-(3,5-difluoro-4-methoxyphenyl)-2-methoxypyridine-3-methanol;

5-[4-(aminosulfonyl)phenyl]-2-butoxy-6-(4-methylphenyl)pyridine-3-methanol;

5-[4-(aminosulfonyl)phenyl]-2-butoxy-6-(3-methylphenyl)pyridine-3-methanol;

5-[4-(aminosulfonyl)phenyl]-2-butoxy-6-(3-methoxyphenyl)pyridine-3-methanol;

5-[4-(aminosulfonyl)phenyl]-2-butoxy-6-(4-methylthiophenyl)pyridine-3-methanol;

5-[4-(aminosulfonyl)phenyl]-2-butoxy-6-(3-methylthiophenyl)pyridine-3-methanol;

5-[4-(aminosulfonyl)phenyl]-2-butoxy-6-(3-chloro-4-methoxyphenyl)pyridine-3-methanol;

5-[4-(aminosulfonyl)phenyl]-2-butoxy-6-(3-fluoro-4-methoxyphenyl)pyridine-3-methanol;

4-[5-cyano-2-(4-tluorophenyl)-6-fluoro-3-pyridyl]benzensulfonamide;

4-[6-bromo-5-cyano-2-(4-fluorophenyl)-3-pyridyl]benzensulfonamide;

4-[5-cyano-2-(4-fluorophenyl)-6-methoxy-3-pyridyl]benzensulfonamide;

4-[5-cyano-6-ethoxy-2-(4-fluorophenyl)-3-pyridyl]benzensulfonamide;

4-[6-butoxy-5-cyano-2-(4-fluorophenyl)-3-pyridyl]benzensulfonamide;

4-[5-cyano-2-(4-fluorophenyl)-6-hexyloxy-3-pyridyl]benzensulfonamride;

4-[5-cyano-2-(4-fluorophenyl)-6-benzyloxy-3-pyridyl]benzensulfonamide;

4-[5-cyano-6-(4-chlorobenzyloxy)-2-(4-fluorophenyl)-3-pyridyl]benzensulfonamide;

4-[5-cyano-2-(4-fluorophenyl)-6-(4-fluorobenzyloxy)-3-pyridyl]benzensulfonamide;

4-[5-cyano-2-(4-fluorophenyl)-6-(4-methoxybenzyloxy)-3-pyridyl]benzensulfonamide;

4-[5-cyano-2-(4-fluorophenyl)-6-(3-quinolylmethoxy)-3-pyridyl]benzensulfonamide;

4-[5-cyano-2-(4-fluorophenyl)-6-(3-pyridylmethoxy)-3-pyridyl]benzensulfonamide;
4-[5-cyano-2-(4-fluorophenyl)-6-(2-thienylmethoxy)-3-pyridyl]benzensulfonamide;
4-[5-cyano-2-(4-fluorophenyl)-6-(2-furylmethoxy)-3-pyridyl]benzensulfonamide;
4-[5-cyano-2-(4-fluorophenyl)-6-(phenylethoxy)-3-pyridyl]benzensulfonamide;
4-[6-(allyloxy)-5-cyano-2-(4-fluorophenyl)-3-pyridyl]benzensulfonamide;
4-[5-cyano-6-(cyclohexylmethoxy)-2-(4-fluorophenyl)-3-pyridyl]benzensulfonamide;
4-[5-cyano-6-(cyclopropylmethoxy)-2-(4-fluorophenyl)-3-pyridyl]benzensulfonamide;
4-[5-cyano-6-(cyclobutylmethoxy)-2-(4-fluorophenyl)-3-pyridyl]benzensulfonamide;
4-[5-cyano-6-(cyclopentylmethoxy)-2-(4-fluorophenyl)-3-pyridyl]benzensulfonamide;
4-[5-cyano-2-(4-fluorophenyl)-6-(3-methyl-2-butenyloxy)-3-pyridyl]benzensulfonamide;
4-[5-cyano-2-(4-fluorophenyl)-6-(phenylcarbonylmethoxy)-3-pyridyl]benzensulfonamide;
4-[5-cyano-2-(4-fluorophenyl)-6-(methoxycarbonylmethoxy)-3-pyridyl]benzensulfonamide;
4-[6-(butoxycarbonylmethoxy)-5-cyano-2-(4-fluorophenyl)-3-pyridyl]benzensulfonamide;
4-[5-cyano-6-(N,N-dimethylaminocarbamylmethoxy)-2-(4-fluorophenyl)-3-pyridyl]benzensulfonamide;
4-[6-(3-chlorobenzylthio)-5-cyano-2-(4-fluorophenyl)-3-pyridyl]benzensulfonamide;
4-[5-cyano-6-(4-fluorobenzylthio)-2-(4-fluorophenyl)-3-pyridyl]benzensulfonamide;
4-[5-cyano-2-(4-fluorophenyl)-6-(2-ouinolylmethylthio)-3-pyridyl]benzensulfonamide;
4-[5-cyano-2-(4-fluorophenyl)-6-(3-pyridylmethylthio)-3-pyridyl]benzensulfonamide;
4-[5-cyano-2-(4-fluorophenyl)-6-(2-thienylmethylthio)-3-pyridyl]benzensulfonamide;
4-[5-cyano-2-(4-fluorophenyl)-6-(3-furylmethylthio)-3-pyridyl]benzensulfonamide;
4-[5-cyano-2-(4-fluorophenyl)-6-(3-phenylethylthio)-3-pyridyl]benzensulfonamide;
4-[6-(allylthio)-5-cyano-2-(4-fluorophenyl)-3-pyridyl]benzensulfonamide;
4-[5-cyano-6-(cyclohexylmethylthio)-2-(4-fluorophenyl)-3-pyridyl]benzensulfonamide;
4-[5-cyano-6-(cyclopentylmethylthio)-2-(4-fluorophenyl)-3-pyridyl]benzensulfonamide;
4-[5-cyano-2-(4-fluorophenyl)-6-(phenylcarbonylmethylthio)-3-pyridyl]benzensulfonamide;
4-[5-cyano-2-(4-fluorophenyl)-6-(ethoxycarbonyimethylthio)-3-pyridyl]benzensulfonamide;
4-[5-cyano-6-[N-(4-chlorobenzyl)amino]-2-(4-fluorophenyl)-3-pyridyl]benzensulfonamide;
4-[5-cyano-6-[N-(2-fluorobenzyl)amino]-2-(4-fluorophenyl)-3-pyridyl]benzensulfonamide;
4-[5-cyano-2-(4-fluorophenyl)-6-[N-(3-methoxybenzyl)amino]-3-pyridyl]benzensulfonamide;
4-[5-cyano-2-(4-fluorophenyl)-6-[N-(4-pyridylmethyl)amino]-3-pyridyl]benzensulfonamide;
4-[5-cyano-2-(4-fluorophenyl)-6-[N-(3-thienylmethyl)amino]-3-pyridyl]benzensulfonamide;
4-[5-cyano-2-(4-fluorophenyl)-6-[N-(2-furylmethyl)amino]-3-pyridyl]benzensulfonamide;
4-[5-cyano-2-(4-fluorophenyl)-6-[N-(4-phenylethyl)amino]-3-pyridyl]benzensulfonamide;
4-[6-[N-(allyl)amino]-5-cyano-2-(4-fluorophenyl)-3-pyridyl]benzensulfonamide;
4-[5-cyano-6-[N-(cyclohexylmethyl)amino]-2-(4-fluorophenyl)-3-pyridyl]benzensulfonamide;
4-[5-cyano-2-(4-fluorophenyl)-6-[N-(phenylcarbonylmethyl)amino]-3-pyridyl]benzensulfonamide;
4-[5-cyano-2-(4-fluorophenyl)-6-[N-(ethoxycarbonylmethyl)amino]-3-pyridyl]benzensulfonamide;
2-methoxy-6-(4-methylphenyl)-5-[4-(methylsulfonyl)phenyl]pyridine-3-carbonitrile;
6-(3-chlorophenyl)-2-methoxy-5-[4-(methylsulfonyl)phenyl]pyridine-3-carbonitrile;
2-methoxy-6-(3,4-methylenedioxyphenyl)-5-[4-(methylsulfonyl)phenyl]pyridine-3-carbonitrile;
6-(3-fluorophenyl)-2-methoxy-5-[4-(methylsulfonyl)phenyl]pyridine-3-carbonitrile;
6-(4-cyanophenyl)-2-methoxy-5-[4-(nmethylsulfonyl)phenyl]pyridine-3-carbonitrile;
6-(4-hydroxyphenyl)-2-methoxy-5-[4-(methylsulfonyl)phenyl]pyridine-3-carbonitrile;
2-methoxy-6-(4-methoxycarbonylphenyl)-5-[4-(methylsulfonyl)phenyl]pyridine-3-carbonitrile;
6-(4-hydroxymethylphenyl)-2-methoxy-5-[4-(methylsulfonyl)phenyl]pyridine-3-carbonitrile;
6-(4-aminophenyl)-2-methoxy-5-[4-(methylsulfonyl)phenyl]pyridine-3-carbonitrile;
6-(4-N,N-dimethylaminophenyl)-2-methoxy-5-[4-(methylsulfonyl)phenyl]pyridine-3-carbonitrile;
2-methoxy-5-[4-(methylsulfonyl)phenyl]-6-(4-phenylaminophenyl)pyridine-3-carbonitrile;
2-methoxy-5-[4-(methylsulfonyl)phenyl]-6-(4-nitrophenyl)pyridine-3-carbonitrile;
2-methoxy-5-[4-(methylsulfonyl)phenyl]-6-(4-trifluoromethoxyphenyl)pyridine-3-carbonitrile;
2-methoxy-6-(4-methoxy-3-fluorophenyl)-5-[4-(methylsulfonyl)phenyl]pyridine-3-carbonitrile;
2-methoxy-6-phenyl-5-[4-(methylsulfonyl)phenyl]pyridine-3-carbonitrile;
2-methoxy-5-[4-(methylsulfonyl)phenyl]-6-[4-(trifluoromethyl)phenyl]pyridine-3-carbonitrile;
6-(4-bromophenyl)-2-methoxy-5-[4-(methylsulfonyl)phenyl]pyridine-3-carbonitrile;
6-(2-chlorophenyl)-2-methoxy-5-[4-(methylsulfonyl)phenyl]pyridine-3-carbonitrile;
6-(4-ethylphenyl)-2-methoxy-5-[4-(methylsulfonyl)phenyl]pyridine-3-carbonitrile;
6-(4-butylphenyl)-2-methoxy-5-[4-(methylsulfonyl)phenyl]pyridine-3-carbonitrile;
6-[4-(difluoromethyl)phenyl]-2-methoxy-5-[4-(methylsulfonyl)phenyl]pyridine-3-carbonitrile;
6-(4-butoxyphenyl)-2-methoxy-5-[4-(methylsulfonyl)phenyl]pyridine-3-carbonitrile;
2-methoxy-5-[4-(methylsulfonyl)phenyl]-6-[4-(methylthio)phenyl]pyridine-3-carbonitrile;
2-methoxy-6-(4-methoxy-3,5-dichlorophenyl)-5-[4-(methylsulfonyl)phenyl]pyridine-3-carbonitrile;
2-methoxy-6-(4-methyl-3,5-difluorophenyl)-5-[4-(methylsulfonyl)phenyl]pyridine-3-carbonitrile;
6-(2,4-dichlorophenyl)-2-methoxy-5-[4-(methylsulfonyl)phenyl]pyridine-3-carbonitrile;
6-(3,4-dichlorophenyl)-2-methoxy-5-[4-(methylsulfonyl)phenyl]pyridine-3-carbonitrile;
2-methoxy-5-[4-(methylsulfonyl)phenyl]-6-[4-(trifluoromethyl)phenyl]pyridine-3-carbonitrile;

6-(3,4-dimethylphenyl)-2-methoxy-5-[4-(methylsulfonyl)
phenyl]pyridine-3-carbonitrile;
6-(3,5-dimethyl-4-methoxyphenyl)-2-methoxy-5-[4-
(methylsulfonyl)phenyl]pyridine-3-carbonitrile;
4-[5-cyano-6-methoxy-2-(4-methylphenyl)-3-pyridyl]
benzensulfonamide;
4-[2-(3-chlorophenyl)-5-cyano-6-methoxy-3-pyridyl]
benzensulfonamide;
4-[5-cyano-6-methoxy-2-(3,4-methylenedioxyphenyl)-3-
pyridyl]benzensulfonamide;
4-[5-cyano-6-methoxy-2-(4-methoxyphenyl)-3-pyridyl]
benzensulfonamide;
4-[5-cyano-2-(4-cyanophenyl)-6-methoxy-3-pyridyl]
benzensulfonamide;
4-[5-cyano-2-(4-hydroxyphenyl)-6-methoxy-3-pyridyl]
benzensulfonamide;
4-[5-cyano-2-(4-hydroxymethylphenyl)-6-methoxy-3-
pyridyl]benzensulfonamide;
4-[2-(4-aminophenyl)-5-cyano-6-methoxy-3-pyridyl]
benzensulfonamide;
4-[5-cyano-2-[4-(N,N-dimethylamino)phenyl]-6-
nmethoxy-3-pyridyl]benzensulfonamide;
4-[5-cyano-6-methoxy-2-(4-methoxycarbonylphenyl)-3-
pyridyl]benzensulfonamide;
4-[5-cyano-6-methoxy-2-(4-
trifluoromethoxycarbonylphenyl)-3-pyridyl]
benzensulfonamide;
4-[5-cyano-6-methoxy-2-(4-phenylaminophenyl)-3-
pyridyl]benzensulfonamide;
4-[5-cyano-6-methoxy-2-(4-nitrophenyl)-3-pyridyl]
benzensulfonamide;
4-[5-cyano-2-(3-fluorophenyl)-6-methoxy-3-pyridyl]
benzensulfonamide;
4-[5-cyano-2-(4-fluorophenyl)-6-methoxy-3-pyridyl]
benzensulfonamide;
4-[5-cyano-2-(3-fluoro-4-methoxyphenyl)-6-methoxy-3-
pyridyl]benzensulfonamide;
4-[5-cyano-6-methoxy-2-phenyl-3-pyridyl]
benzensulfonamide;
4-[5-cyano-6-methoxy-2-[4-(trifluoromethyl)phenyl]-3-
pyridyl]benzensulfonamide;
4-[2-(4-bromophenyl)-5-cyano-6-methoxy-3-pyridyl]
benzensulfonamide;
4-[2-(2-chlorophenyl)-5-cyano-6-methoxy-3-pyridyl]
benzensulfonamide;
4-[5-cyano-2-(4-ethylphenyl)-6-methoxy-3-pyridyl]
benzensulfonamide;
4-[2-(4-butylphenyl)-5-cyano-6-methoxy-3-pyridyl]
benzensulfonamide;
4-[5-cyano-2-[4-(difluoromethyl)phenyl]-6-methoxy-3-
pyridyl]benzensulfonamide;
4-[2-(4-butoxyphenyl)-5-cyano-6-methoxy-3-pyridyl]
benzensulfonamide;
4-[5-cyano-6-methoxy-2-[4-(methylthio)phenyl]-3-pyridyl]
benzensulfonamide;
4-[5-cyano-6-methoxy-2-(4-methoxy-3,5-dichlorophenyl)-
3-pyridyl]benzensulfonamide;
4-[5-cyano-6-methoxy-2-(4-methyl-3,5-difluorophenyl)-3-
pyridyl]benzensulfonamide;
4-[5-cyano-2-(2,4-dichlorophenyl)-6-methoxy-3-pyridyl]
benzensulfonamide;
4-[5-cyano-2-(3,4-dichlorophenyl)-6-methoxy-3-pyridyl]
benzensulfonamide;
4-[5-cyano-2-(3,4-dimethylphenyl)-6-methoxy-3-pyridyl]
benzensulfonamide;
4-[5-cyano-2-(3,5-dimethyl-4-methoxyphenyl)-6-methoxy-
3-pyridyl]benzensulfonamide;

6-(4-fluorophenyl)-2-methoxy-5-[4-(methylsulfonyl)
phenyl]pyridine-3-carbonitrile;
2-bromo-6-(4-fluorophenyl)-5-[4-(methylsulfonyl)phenyl]
pyridine-3-carbonitrile;
6-(4-fluorophenyl)-5-[4-(methylsulfonyl)phenyl]-2-
phenylpyridine-3-carbonitrile;
2-chloro-6-(4-fluorophenyl)-5-[4-(methylsulfonyl)phenyl]
pyridine;
2-methylthio-6-[4-(methylthio)phenyl]-5-[4-
(methylsulfonyl)phenyl]pyridine;
2-azido-6-(4-fluorophenyl)-5-[4-(methylsulfonyl)phenyl]
pyridine;
6-(4-fluorophenyl)-5-[4-(methylsulfonyl)phenyl]-2-
propoxypyridine-3-carbonitrile;
2-methoxy-6-(4-methoxyphenyl)-5-[4-(methylsulfonyl)
phenyl]pyridine-3-carbonitrile;
2-(dimethylamino)-6-(4-fluorophenyl)-5-[4-
(methylsulfonyl)phenyl]pyridine-3-carbonitrile;
6-(4-fluorophenyl)-5-[4-(methylsulfonyl)phenyl]-2-
(methylthio)pyridine-3-carbonitrile;
2-butoxy-6-(4-fluorophenyl)-5-[4-(methylsulfonyl)phenyl]
pyridine-3-carbonitrile;
6-(4-fluorophenyl)-5-[4-(methylsulfonyl)phenyl]-2-
(phenylmethoxy)pyridine-3-carbonitrile;
6-(4-fluorophenyl)-2-(methylamino)-5-[4-(methylsulfonyl)
phenyl]pyridine-3-carbonitrile;
6-(4-fluorophenyl)-5-[4-(methylsulfonyl)phenyl]-2-[(2-
propenyl)oxy]pyridine-3-carbonitrile;
6-(4-fluorophenyl)-2-hexyloxy-5-[4-(methylsulfonyl)
phenyl]pyridine-3-carbonitrile;
6-(4-fluorophenyl)-5-[4-(methylsulfonyl)phenyl]-2-
pentoxypyridine-3-carbonitrile;
2-chloro-6-(4-fluorophenyl)-5-[4-(methylsulfonyl)phenyl]
pyridine-3-carbonitrile;
6-(4-fluorophenyl)-2-hydroxy-5-[4-(methylsulfonyl)
phenyl]pyridine-3-carbonitrile;
2-chloro-6-(4-fluorophenyl)-5-[4-(methylsulfonyl)phenyl]-
3-pyridinecarboxamide; and
6-(4-fluorophenyl)-5-[4-(methylsulfonyl)phenyl]-3-
pyridinecarbonitrile.

Within Formula I there is a subclass of compounds of high interest represented by Formula II:

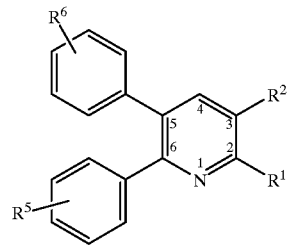

(II)

wherein $R^1$ is selected from hydrido, halo, alkoxy, haloalkoxy, aryl, alkylthio, alkylamino, aralkoxy, azido and alkenyloxy; wherein $R^2$ is selected from hydrido, cyano, hydroxyalkyl, haloalkyl, aminoalkyl, alkylaminoalkyl, alkylcarbonyloxyalkyl, aminocarbonyl and alkylcarbonylaminoalkyl; and wherein $R^5$ and $R^6$ are one or more radicals independently selected from halo, alkylsulfonyl, aminosulfonyl, alkoxy and alkylthio; provided one of $R^5$ and $R^6$ is alkylsulfonyl, aminosulfonyl, or haloalkylsulfonyl; or a pharmaceutically-acceptable salt thereof.

A preferred class of compounds consists of those compounds of Formula II wherein $R^1$ is selected from hydrido, halo, lower alkoxy, lower haloalkoxy, aryl selected from phenyl, naphthyl and biphenyl, lower alkylthio, lower alkylamino, lower aralkoxy, azido and lower alkenyloxy; wherein $R^2$ is selected from hydrido, cyano, lower hydroxyalkyl, lower haloalkyl, lower aminoalkyl, lower alkylcarbonyloxyalkyl, aminocarbonyl and lower alkylcarbonylaminoalkyl; and wherein $R^5$ and $R^6$ are one or more radicals independently selected from halo, lower alkylsulfonyl, aminosulfonyl, lower alkoxy and lower alkylthio; or a pharmaceutically-acceptable salt thereof.

A class of compounds of particular interest consists of those compounds of Formula II wherein $R^1$ is selected from hydrido, fluoro, chloro, bromo, iodo, methoxy, ethoxy, isopropoxy, tert-butoxy, propoxy, butoxy, isobutoxy, pentoxy, trifluoromethoxy, 4,4,4-trifluorobutoxy, 3,3,3-trifluoropropoxy, phenyl, naphthyl, methylthio, methylamino, dimethylamino, N-ethyl-N-methylamino, benzyloxy, phenylethoxy, azido, and 3-methyl-2-butenyloxy; wherein $R^2$ is selected from hydrido, cyano, hydroxymethyl, 1-methylmethanol, trifluoromethyl, difluoromethyl, fluoromethyl, aminomethyl, N,N-dimethylaminomethyl, N-methylaminomethyl, methylcarbonyloxymethyl, propylcarbonyloxymethyl, propylcarbonyloxyethyl, tert-butylcarbonyloxymethyl, aminocarbonyl and methylcarbonylaminomethyl; and wherein $R^5$ and $R^6$ are one or more radicals independently selected from fluoro, chloro, bromo, iodo, methylsulfonyl, ethylsulfonyl, aminosulfonyl, methoxy, ethoxy, isopropoxy, tert-butoxy, propoxy, butoxy, isobutoxy, pentoxy, methylenedioxy, ethylthio and methylthic.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals, having at least one carbon-carbon double bond, of two to about twenty carbon atoms or, preferably, two to about twelve carbon atoms. More preferred alkyl radicals are "lower alkenyl" radicals having two to about six carbon atoms. Examples of lower alkenyl radicals include ethenyl, propenyl, allyl, butenyl and 4-methylbutenyl. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1≠6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms, any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide "haloalkoxy" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cycloalkylalkoxy" embraces radicals having cycloalkyl radicals, as defined above, attached to an alkoxy radical. The term "alkenyloxy" embraces radicals having alkenyl portions of two to about ten carbon atoms attached to an oxygen atom. More preferred alkenyloxy radicals are "lower alkenyloxy" radicals having two to six carbon atoms. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indanyl and biphenyl. The term "heterocyclo" embraces saturated, partially saturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); and saturated 3 to 6-membered heteromonocyclic group containing 1 to 2 sulfur atoms and 1 to 3 nitrogen atoms (e.g., thiazolidinyl, etc.). Examples of partially saturated heterocyclo radicals include dihydrothiophene, dihydropyran, dihydrofuran and dihydrothiazole. The term "heteroaryl" embraces unsaturated heterocyclo radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclic group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclic group containing 1 to 2 sulfur atoms and 1 to 3 nitrogen atoms (e.g., benzothiazolyl, benzothiadiazolyl, etc.) and the like. The term also embraces radicals where heterocyclo radicals are fused with aryl radicals. Examples of such fused bicyclic radicals include benzofuran, benzothiophene, and the like. Said heterocyclo radical may have 1 to 3 substituents such as lower alkyl, hydroxy, oxo, amino and lower alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "cycloalkylalkylthio" embraces radicals having cycloalkyl radicals, as defined above, attached to an alkylthio radical. More preferred cycloalkylalkylthio radicals are "lower cycloalkylalkylthio" radicals having cycloalkyl radicals of three to six carbon atoms. The term "alkenylthio" embraces radicals containing a linear or branched alkenyl radical, of two to about ten carbon atoms attached to a divalent sulfur atom. More preferred alkenylthio radicals are "lower alkenythio" radicals having alkenyl radicals of two to six carbon atoms. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyll" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. The terms "carboxy" or "carboxyl", whether used alone or with other terms, such as "carboxyalkyl", denotes —CO$_2$H. The term "carbonyl", whether used alone or with other terms, such as "alkoxycarbonyl", denotes —(C=O)—. The term "alkoxycarbonyl" denotes a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals and preferably "phenylalkyl" radicals, such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "arylalkenyl" embraces aryl-substituted alkenyl radicals such as phenylallyl. The term "heteroaralkyl" embraces heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "arylalkenyloxy" embraces arylalkenyl radicals attached through an oxygen atom to other radicals. The term "aralkylthio" embraces aralkyl radicals attached to a sulfur atom. The term "aralkylthioalkyl" embraces aralkylthio radicals attached through a sulfur atom to an alkyl radical. The term "heteroaralkoxy" embraces heteroaralkyl radicals attached through an oxygen atom to other radicals. The term "heteroaralkylthio" embraces heteroaralkyl radicals attached through a sulfur atom to other radicals. The term "aminoalkyl" embraces alkyl radicals substituted with amino radicals. The term,alkylamino denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkenylamino" denotes amino groups which have been substituted with one or two alkenyl radicals, as defined above. The term "cycloalkylamino" denotes amino groups which have been substituted with one or two cycloalkyl radicals, as defined above. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The term "heteroaralkylamino" embraces heteroaralkyl radicals, as defined above, attached through an nitrogen atom to other radicals. The terms "N-arylaminoalkyl" and "N-aryl-N-alkylaminoalkyl" denote aminoalkyl groups which have been substituted with one aryl radical or one aryl and one alkyl radical, respectively. Examples of such radicals include N-phenylaminomethyl and N-phenyl-N-methylaminomethyl. The term "aminocarbonyl" denotes an amide group of the formula —C(=O)NH$_2$. The term "alkylaminocarbonylalkoxy" denotes an aminocarbonyl group which has been substituted with one or two alkyl radicals on the amino nitrogen atom, attached to an alkoxy radical. The term "alkylaminocarbonylalkylthio" denotes an aminocarbonyl group which has been substituted with one or two alkyl radicals on the amino nitrogen atom, attached to an alkylthio radical. The term "arylcarbonylalkoxy" embraces radicals having one or more arylcarbonyl radicals attached to an alkoxy radical. The term "arylcarbonylalkylamino" embraces radicals having one or more arylcarbonyl radicals attached to an alkylamino radical. The term "arylcarbonylalkylthio" embraces radicals having one or more arylcarbonyl radicals attached to an alkylthio radical. The term "alkoxycarbonylalkoxy" embraces radicals having one or more alkoxycarbonyl radicals attached to an alkoxy radical. The term "alkoxycarbonylalkylaminoll embraces radicals having one or more alkoxycarbonyl radicals attached to an alkylamino radical. The term "alkoxycarbonylalkylthio" embraces radicals having one or more alkoxycarbonyl radicals attached to an alkylthio radical. The term "alkylcarbonylaminoalkyl" embraces radicals having one or more alkyl radicals attached to a carbonyl radical further attached to an aminoalkyl radical. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom. The term "alkylcarbonyloxyalkyl" embraces radicals having one or more alkylcarbonyl radicals attached through any oxygen atom to an alkyl radical.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising treating the subject having such inflammation or disorder with a therapeutically-effective amount of a compound of Formula I.

Also included in the family of compounds of Formula I are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Racemic alcohol-containing compounds may be resolved to their single enantiomers by the following procedure. Treatment of the racemic alcohols with an acetylating agent, such as vinyl acetate or isopropenyl acetate, in the presence of an appropriate enzyme results in the selective acetylation of one of the constituent enantiomeric alcohols, leading to a crude product consisting of essentially enantiomerically pure alcohol. Appropriate enzymes include, but are not limited to, lipases (such as AMANO Lipase PS30), cholinesterases and proteases. The reaction may be monitored to complete acetylation of one of the enantiomers using HPLC. The enantiomerically pure alcohol may be separated from enantiomerically pure acetate by column chromatography. Saponification of the acetate using aqueous base provides the other enantiomerically pure alcohol.

Alternatively, alcohols can be resolved via procedures outlined in E. Eliel and S. Wilen, *Stereochemistry of Organic compounds*, 337–340 (1994).

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VIII, wherein the $R^1$–$R^6$ substituents are as defined for Formula I–II, above, except where further noted.

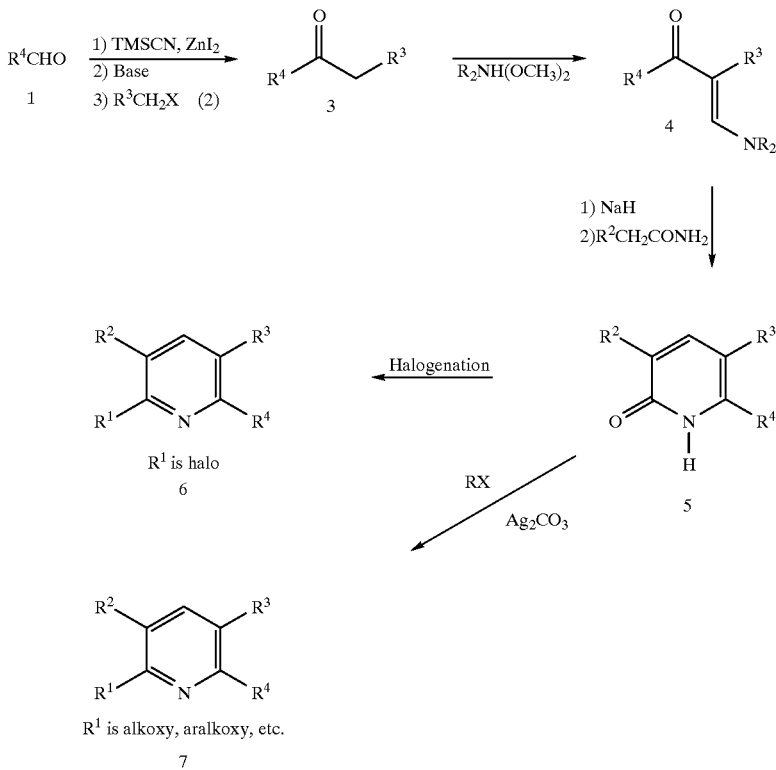

Scheme I

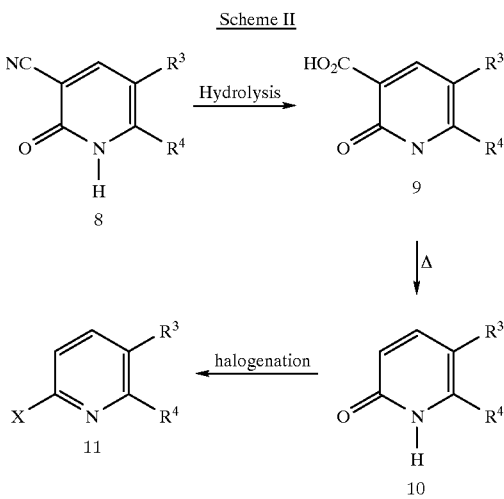

Scheme II

Scheme I shows the multi-step method to form the 2,3-substituted pyridines 6 of the current invention. In step 1, a silylating agent such as trimethylsilyl cyanide to a substituted aldehyde 1 ($R^4CHO$) in a solvent such as dichloromethane. After the addition is complete, zinc iodide is added to give the protected ketone. The protected ketone is added to a solution of base such as a lithium amide reagent (i.e. lithium bis(trimethylsilyl)amide) in an appropriate solvent such as tetrahydrofuran. After stirring, a solution of the halo compound 2 (where X is halo) in an appropriate solvent, such as tetrahydrofuran, is added. Treatment with aqueous hydrochloric acid followed by treatment with aqueous base, such as sodium hydroxide, to yield the ketone 3. In step 2, a solution of ketone 3 from step 1 in an appropriate solvent such as dimethylformamide is added to a formamide dimethyl acetal (where R is methyl). The resulting mixture is stirred to give the protected 3-amino-prop-2-en-1-one 4. In step 3, 3-amino-prop-2-en-1-one 4 from step 2 is added to sodium hydride in mineral oil in a solvent such as dimethylformamide, followed by an acetamide and an alcohol, such as methanol, in dimethylformamide. After heating to about 70° C., the 1,2-dihydro-oxopyridine 5 is isolated. In step 4, a mixture of the 1,2-dihydro-oxopyridine 5 from Step 3 and a halogenating reagent such as phosphorous oxychloride is heated in a bomb to about 200° C. to give the desired 2-halopyridines 6 of the present invention, where $R^1$ is chloro. Oxopyridine 5 can be converted to alkoxy, aralkoxy and alkenyloxy substituted pyridine by treating with silver carbonate and an organohalide ($R^1X$) in a solvent such as acetone or dimethylformamide to give the 2,3-substituted pyridines 7.

Alternatively, halo compound 2 can be prepared by treating a corresponding alcohol with a halogenating agent, such as thionyl chloride.

Synthetic Scheme II describes the three step preparation of 2-halopyridines from the oxo-pyridinecarbonitriles 8 (corresponding to oxopyridine 5 where $R^2$ is cyano). In step 1, the oxo-3-pyridinecarbonitrile 8 is hydrolyzed by treating with a strong acid such as 85% sulfuric acid and heating at a high temperature, such as about 200° C. to give the oxopyridine-3-carboxylic acid 9. In step 2, the oxo-3-pyridinecarboxylic acid 9 from Step 1 is decarboxylated such as by heating at a high temperature such as about 330° C. to give the 1,2-dihydro-oxopyridine 10. In step 3, the 1,2-dihydro-oxopyridine 10 from Step 2 is halogenated with a reagent such as phosphorous oxychloride and heating in an autoclave at a high temperature, such as about 200° C., to give the desired 2-halopyridines 11 of the present invention. Alternatively, the 1,2-dihydro-oxopyridine 10 can be halogenated by treatment with a halogenating agent such as phenylphosphonic dichloride at an elevated temperature. A suitable temperature for this reaction is 200°.

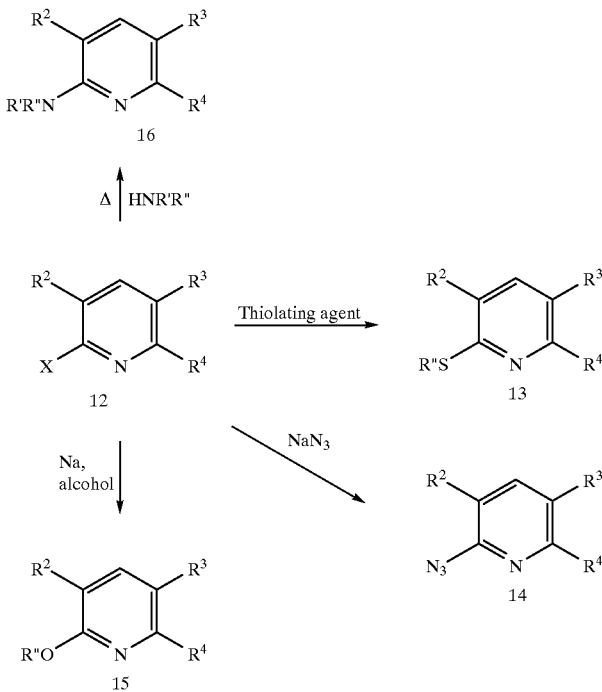

Scheme III details the synthesis of antiinflammatory pyridines of the present invention from 2-halopyridines 12 (where X is halo such as chloro). 2-Alkylthiopyridines 13 can be prepared by adding a thiolating reagent, such as sodium thiomezhoxide, to a solution of 2-halopyridine 12 in a solvent, such as dimethylformamide. Alternatively, the halopyridines 12 can be converted to azidopyridines 14 by adding sodium azide to a solution of 2-halopyridine 12 in a solvent, such as dimethylformamide, and heating at a temperature of about 100° C. Alkoxypyridines 15 can be prepared from halopyridines 12 in two steps. Sodium is first dissolved in an alcohol to form an alkoxide anion. After dissolution is complete, 2-halopyridines 12 are added as a solid, and the resulting mixture is stirred at reflux to yield the alkoxypyridines 15. Aminopyridines 16 can be prepared from halopyridines 12 by direct aminolysis with an appropriate amine and heat. Additionally, aminopyridine 16 (R' and R"=H) can be prepared from azidopyridines 14 by catalytic hydrogenation with a catalyst such as 10% palladium on carbon or by reaction with a reagent such as triphenylphosphine followed by hydrolysis with water.

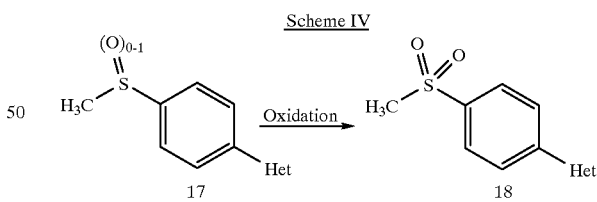

Scheme IV shows a method to form the alkylsulfonylphenyl substituted pyridines 18 of the current invention by oxidation of alkylthio or alkylsulfinyl derivatives 17. Aqueous hydrogen peroxide (30%) is added to a suspension of a (methylthio)phenyl substituted pyridine 17 in acetic acid. The mixture is stirred while heating to about 100° C. for about 2 hours. Alternatively, m-chloroperoxybenzoic acid (MCPBA), and other oxidizing agents can be used to form the sulfonyl radicals 18.

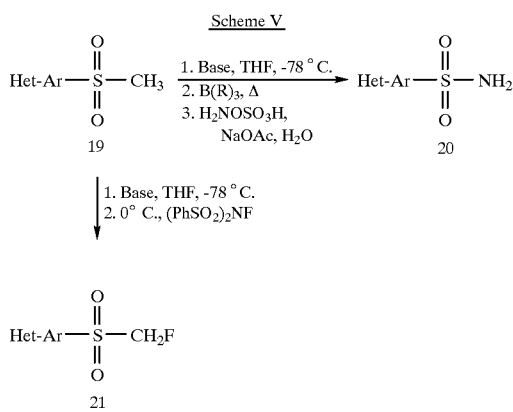

Synthetic Scheme V shows the three step procedure used to prepare sulfonamide antiinflammatory agents 20 and the two step procedure used to prepare fluoromethyl sulfone antiinflammatory agents 21 from their corresponding methyl sulfones 19. In step one, THF solutions of the methyl sulfones 19 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. An alternative to the boron chemistry involves room temperature alkylation, such as with haloalkyltrialkylsilanes, followed by treatment with silylalkyl-elimination agents. In step three, an aqueous solution of sodium acetate and hydroxylamine-O-sulfonic acid is added to provide the corresponding sulfonamide antiinflammatory agents 20 of this invention. Alternatively, the anion solutions generated in step one may be warmed to 0° C. and treated with N-fluorodibenzenesulfonamide to provide the corresponding fluoromethyl sulfone antiinflammatory agents 21 of this invention.

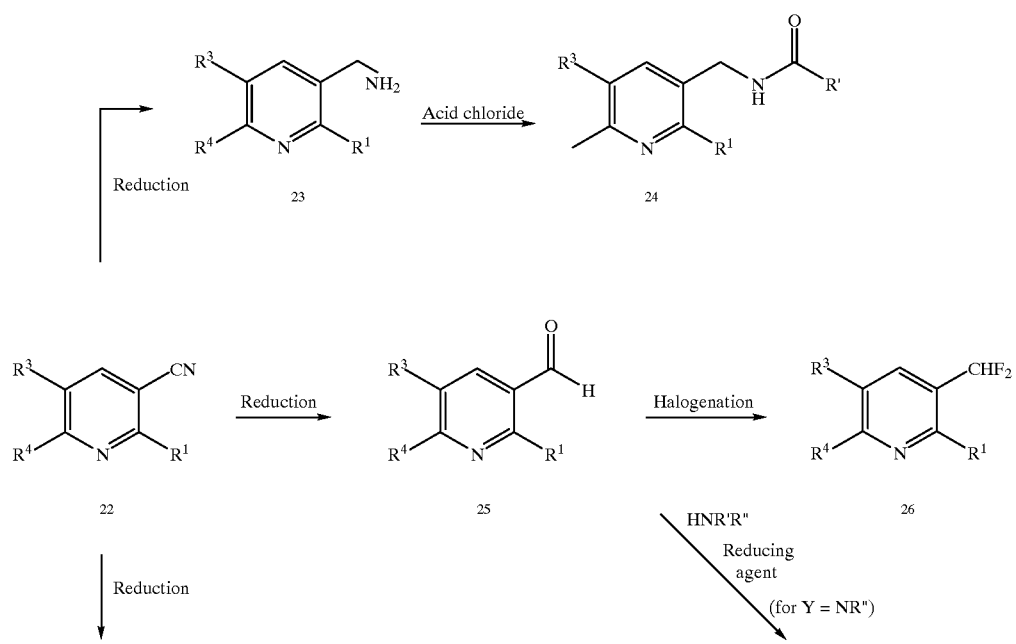

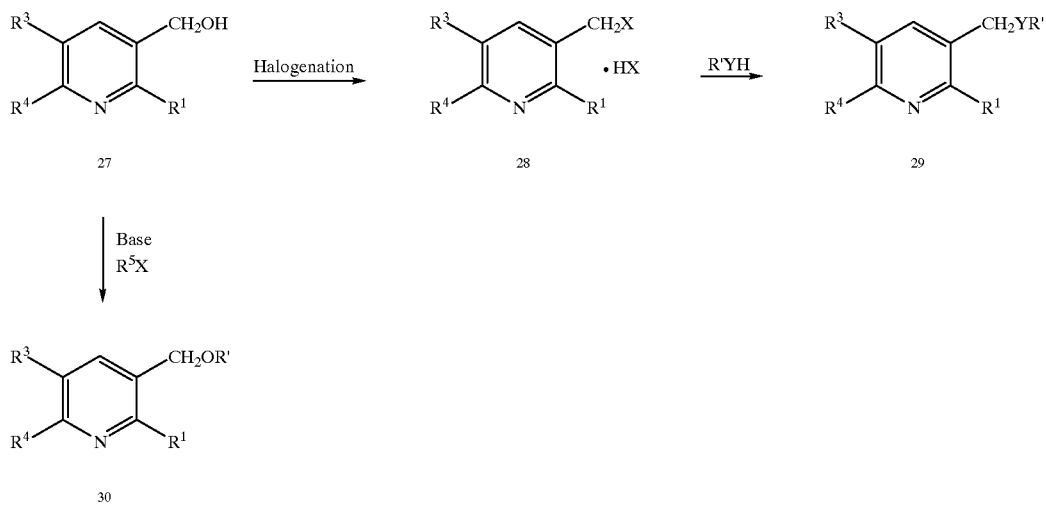

Synthetic Scheme VI shows the procedure used to prepare 3-alkylcarbonylaminoalkyl pyridine antiinflammatory agents 24, 3-haloalkyl pyridine antiinflammatory agents 26, 3-hydroxyalkyl pyridine antiinflammatory agents 27, heteroatom substituted 3-alkyl pyridine antiinflammatory agents 29 and 3-aryloxyalkyl pyridine antiinflammatory agents 30 from the corresponding carbonitriles 22. The 3-alkylcarbonylaminoalkyl pyridine antiinflammatory agents 24 (where R' is alkyl) are prepared in a two step procedure from the carbonitriles 22. In step one, the carbonitrile 22 is reduced using reducing agents, such as diisobutyl aluminum hydride (DIBAL) in a solvent such as toluene or boranes in a solvent such as tetrahydrofuran, at room temperature or reflux to form the aminoalkyl 23. Additional reducing reagent may be added to the solution. In step two, an acid chloride is added to the aminoalkyl 23 in a solvent such as ethyl ether or tetrahydrofuran and stirred to form the alkylcarbonylaminoalkyl pyridines 24. The 3-haloalkyl pyridine antiinflammatory agents 26 are prepared in a two step procedure from the carbonitriles 22. In step one, the carbonitriles 22 are reduced using agents, such as diisobutyl aluminum hydride (DIBAL) in a solvent such as toluene, at room temperature to form the aldehydes 25. The 3-hydroxyalkyl pyridines 27 also can be isolated from this reaction. In step two, a halogenating agent, such as diethylamino sulfur trifluoride (DAST) is added to the aldehyde 25 to form the haloalkyl pyridines 26. Reduction of aldehydes 25 with agents such as diisobutyl aluminum hydride (DIBAL) followed by methanol and water in methanol to yield the 3-hydroxyalkyl pyridines 27. Compound 27 is convertible to alkoxyalkyl, alkylcarbonyloxyalkyl and aralkoxyalkyl compounds 30 by sequential treatment first with a base and then with an alkyl, acyl or aralkyl halide. An example of a suitable base is sodium hydride. Examples of alkyl and aralkyl halides are methyl iodide and benzyl chloride. Alternatively, compound 27 may be converted to the haloalkyl compound 28 using a suitable halogenating agent, such as thionyl chloride. Under such circumstances, the hydrochloride salt may be isolated. This in turn may be converted to compounds 29 by reaction with the appropriate alcohol, thiol, or amine. It may be advantageous to carry out this reaction in the presence of a base. Examples of suitable alcohols are methanol, ethanol, benzyl alcohol and phenol. Examples of suitable thiols are n-butyl mercaptan, benzylthiol and thiophenol. Examples of suitable amines are dimethylamine, benzylamine, N-methylbenzylamine, aniline, N-methylaniline and diphenylamine. Examples of suitable bases are sodium hydride and potassium carbonate. Alternatively, amines are accessible by reaction of aldehyde 25 with a primary or secondary amine in the presence of a reducing agent. Examples of suitable primary amines are methyl amine and ethylamine. An example of a suitable secondary amine is dimethylamine. Suitable reducing agents include sodium cyanoborohydride and sodium borohydride.

Scheme VII

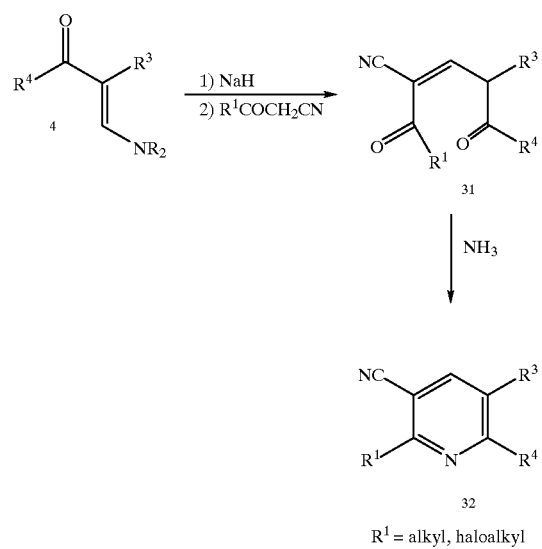

$R^1$ = alkyl, haloalkyl

Scheme VII describes the synthesis of compounds where $R^1$ of Formula I is alkyl or haloalkyl. Intermediate 4 from Scheme I is reacted with the enolate anion of a ketonitrile generated by reacting the ketonitrile with a base, such as sodium hydride. Suitable ketonitriles are cyanoacetone and cyanotrifluoroacetone ($R^1$=$CH_3$ or $CF_3$, respectively, in Scheme VII). The resulting 1,5-diketone 31 is cyclized to pyridine 32 by reaction with ammonia.

Scheme VIII

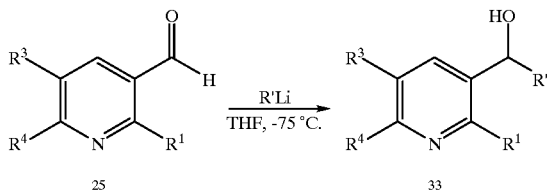

Synthetic Scheme VIII describes the synthesis of alcohols 33 from aldehydes 25 (Scheme VI). Nucleophillic addition via alkyllithium reagents (R'Li) and grignard reagents (R'MgX), and the like, yields the appropriate alcohols 33.

The following examples contain detailed descriptions of the methods of preparation of compounds of Formula I-II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

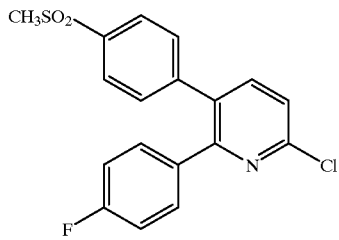

2-Chloro-6-(4-flourophenyl)-5-[4-(methylsulfonyl) phenyl]pyridine

Step 1: Preparation of (4-fluorophenyl)-2-trimethylsilyl-ethanenitrile

To a solution of 50.0 g (403 mMol) of 4-fluorobenzaldehyde in 100 ml of dichloromethane stirring in an ice bath under nitrogen was added dropwise 54 ml (40 g, 403 mMol, 1.0 eq) of trimethylsilyl cyanide. After the addition was complete, 10 mg of anhydrous zinc iodide was added, and stirring continued overnight while the mixture warmed to room temperature. The solvent was removed by distillation under reduced pressure, and continued distillation under high vacuum gave (4-fluorophenyl)-2-trimethylsilyl-ethanenitrile (82.2 g) as a very pale straw yellow liquid: b.p. 81° C. (1 mm).

Step 2: Preparation of (4-methylthiophenyl)chloromethane

To a solution of 50.0 g (325 mMol) of 4-(methylthio) benzyl alcohol in 350 ml of toluene stirring at room temperature under nitrogen, was added 5 drops of pyridine, and then 28.4 ml (46.4 g, 390 mMol, 1.2 eqs) of thionyl chloride was added dropwise. After 3 hours, ice water was added and the mixture was stirred for 20 minutes. The mixture was transferred to a separatory funnel and shaken thoroughly. The organic layer separated and was dried over sodium sulfate, filtered, and evaporated. Distillation of the residue under reduced pressure gave (4-methylthiophenyl) chloromethane (50.54 g) as a colorless liquid: b.p. 89–95° C. (1 mm).

Step 3: Preparation of 1-(4-fluorophenyl)-2-(4-methylthiophenyl)ethan-1-one

To 321 ml of a 1.0M solution of lithium bis(trimethylsilyl) amide in tetrahydrofuran (containing 321 mMol, 1.1 eqs) along with an additional 200 ml of dry tetrahydrofuran stirring at −70° C., was added dropwise a solution of 65.1 g (292 mMol) of (4-fluorophenyl)-2-trimethylsilyl-ethanenitrile from Step 1 in 100 ml of tetrahydrofuran. After stirring for 1 hour, a solution of 50.5 g (292 mMol, 1.0 eq) of (4-methylthiophenyl)chloromethane from Step 2 in 100 ml of tetrahydrofuran. The mixture was stirred overnight while warming to room temperature. To the mixture was then added 300 ml of 3N aqueous hydrochloric acid, and the resulting two phase mixture was stirred for 6 hours. The layers were separated, and the organic layer evaporated. The residue was taken up in 400 ml of dichloromethane, 250 ml of 2N aqueous sodium hydroxide was added, and the resulting two phase mixture was stirred rapidly overnight. The organic layer was separated and 100 ml of dimethylformamide were added. The solution was dried over sodium sulfate, filtered, and evaporated to give a yellow solid. Crystallization of the crude intermediate from ethyl acetate/toluene gave 1-(4-fluorophenyl)-2-( 4-methylthiophenyl) ethan-1-one as white plates (25.8 g). Concentration of the filtrate followed by trituration of the residue gave an additional 15.7 g of white crystals.

Step 4: Preparation of 1-(N,N-dimethylamino)-3-(4-fluorophenyl)-2-(4-methylthiophenyl)prop-1-en-3-one To a solution of 25.8 g (99.2 mMol) of 1-(4-fluorophenyl)-2-(4-methylthiophenyl)ethan-1-one from Step 3 in 200 ml of dimethylformamide was added 33 ml (30 g, 250 mMol) of dimethylformamide dimethyl acetal. The resulting mixture was stirred at 90° C. for 2 hours. Evaporation of the volatiles gave 1-(N,N-dimethylamino)-1-(4-fluorophenyl)-2-(4-methylthiophenyl)prop-1-en-3-one as a yellow solid (32.5 g).

Step 5: Preparation of 12-dihydro-6-(4-fluorophenyl)-5-[4-(methylthio)phenyl]-2-oxo-pyridine-3-carbonitrile To 1.45 g of 60% dispersion of sodium hydride in mineral oil (containing 869 mg, 36.2 mMol), washed once with hexane, in 20 ml of dry dimethylformamide, was added dropwise a solution of 9.42 g (29.9 mMol) of 1-(N,N-dimethylamino)-1-(4-fluorophenyl)-2-(4-methylthiophenyl)prop-1-en-3-one from Step 4, cyanoacetamide (2.59 g, 30.3 mMol), and 2.9 ml of methanol in 50 ml of dimethylformamide. After the addition was complete, the resulting dark solution was stirred overnight at 70–80° C. After cooling, the mixture was added in portions to 500 ml of 1M aqueous sodium dihydrogen phosphate, producing a yellow solid. The solid was filtered, washed with water, and dried to give 9.24 g of 1,2-dihydro-6-(4-fluorophenyl)-5-[4-(methylthio) phenyl]-2-oxo-pyridine-3-carbonitrile.

Step 6: Preparation of 1,2-dihydro-6-(4-fluorophenyl)-5-[4-(methylsulfonyl)phenyl]-2-oxo-pyridine-3-carbonitrile To a suspension of 6.62 g (19.7 mMol) of 1,2-dihydro-6-(4-fluorophenyl)-5-[4-(methylthio)phenyl]-2-oxo-pyridine-3-carbonitrile from Step 5 in 53 ml of acetic acid was added 8.3 ml of 30% aqueous hydrogen peroxide. The mixture was stirred while heating to 100° C. and so maintained for 2 hours. After cooling, the mixture was poured into 350 ml of cold water producing a solid. The solid was filtered, washed with water, and air dried to give 1,2-dihydro-6-(4-fluorophenyl)-5-[4-(methylsulfonyl)phenyl]-2-oxo-pyridine-3-carbonitrile, 6.47 g, as a light tan powder.

Step 7: Preparation of 6-(4-fluorophenyl)-1,2-dihydro-5-[4-(methylsulfonyl)phenyl]-2-oxo-pyridine-3-carboxylic acid A mixture of 6-(4-fluorophenyl)-1,2-dihydro-5-[4-(methylsulfonyl)phenyl]-2-oxo-pyridine-3-carbonitrile of Step 6 (6.47 g, 17.6 mMol) and 85 ml of 85% sulfuric acid was stirred while heating to 200° C. and so maintained for ten minutes. The mixture was cooled, poured into ice and diluted with water. The resulting solid was filtered, washed with water, and dried to give 6-(4-fluorophenyl)-1,2-dihydro-5-[4-(methylsulfonyl)phenyl]-2-oxopyridine-3-carboxylic acid (6.53 g).

Step 8: Preparation of 6-(4-fluorophenyl)-1,2-dihydro-5-[4-(methylsulfonyl)phenyl]-2-oxopyridine 6-(4-Fluorophenyl)-1,2-dihydro-5-[4-(methylsulfonyl)phenyl]-2-oxopyridine-3-carboxylic acid from Step 7 (4.14 g, 11.4 mMol) was heated with stirring to about 325° C. until melted, and then at 330° C. until gas evolution ceased. The material solidified upon cooling to give 6-(4-fluorophenyl)-1,2-dihydro-5-[4-(methylsulfonyl)phenyl]-2-oxopyridine as a black solid.

Step 9: Preparation of 2-chloro-6-(4-fluorophenyl)-5-[4-(methylsulfonyl)-phenyl]-pyridine A mixture of 1.00 g (2.92 mMol) of 6-(4-fluorophenyl)-1,2-dihydro-5-[4-(methylsulfonyl)phenyl]-2-oxopyridine from Step 8 and 25 ml of phosphorous oxychloride was heated in a bomb to 200° C. and maintained for 3 hours. After cooling, the mixture was evaporated to dryness. Chromatography of the residue over silica gel using 50% ethyl acetate/hexane as eluent gave 2-chloro-6-(4-fluorophenyl)-5-[4-(methylsulfonyl)phenyl]pyridine (211 mg) as a pure white crystalline solid: m.p. 192° C. (DSC). Anal. Calc'd for $C_{18}H_{13}ClFNO_2S \cdot \frac{1}{4} H_2O$ (MW 366.33): C, 59.02; H, 3.58; N, 3.82. Found: C, 58.68; H, 3.65; N, 3.86.

EXAMPLE 2

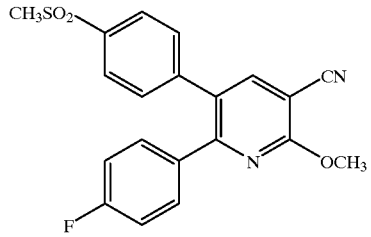

6-(4-Fluorophenyl)-2-methoxy-5-[4-(methylsulfonyl)phenyl]-pyridine-3-carbonitrile Step 1: Preparation of 1-(N,N-dimethylamino)-3-(4-fluorophenyl)-2-[4-(methylthio)phenyl]prop-1-en-3-one To a 500 ml 2-necked flask fitted with a thermometer and magnetic stirrer was added 20 g (76.9 mMol) of 1-(4-fluorophenyl)-2-(4-(methylthio)phenyl)ethan-1-one, Example 1, Step 3, 18.3 g (154 mMol) of dimethylformamide dimethyl acetal and 50 ml dry dimethylformamide (DMF). The reaction mixture was heated to 75° C. for 3 hours, cooled to room temperature and evaporated to dryness and to recover 26.1 g a yellowish orange solid.

Step 2: Preparation of 1,2-dihydro-6-(4-fluorophenyl)-5-[4-(methylthio)phenyl]-2-oxo-pyridine-3-carbonitrile A solution of 26.1 g of 1-(N,N-dimethylamino)-3-(4-fluorophenyl)-2-[4-(methylthio)phenyl]prop-1-en-3-one (Step 1), 200 ml of dry DMF, 7.2 g (8.6 mMol) of the cyanoacetamide and 8 ml methanol was transferred to a dropping funnel. This solution was added dropwise to a slurry of 4.0 g of sodium hydride in 100 ml of DMF in a 3-necked round bottom flask with a magnetic stirrer and cooled with an ice bath. The temperature reached to 25° C. After complete addition of the reactants the mixture was heated to 80° C. for 4 hours, cooled and poured into one liter of 1M $NaH_2PO_4$ to give an insoluble yellow solid which was washed with water and air dried to yield 24.5 g of a yellow powder (95%).

Step 3: Preparation of 1,2-dihydro-6-(4-fluorophenyl)-5-[4-(methylsulfonyl)phenyl]-2-oxo-pyridine-3-carbonitrile To a mixture of 1,2-dihydro-6-(4-fluorophenyl)-5-[4-(methylthio)phenyl]-2-oxo-pyridine-3-carbonitrile (Step 2) (24.5 g, 72.9 mMol) and 200 ml acetic acid in a 1000 ml flask with a magnetic stirrer was added 30 ml of 30% hydrogen peroxide. The mixture was heated 5 hours at 100° C. After cooling to room temperature, an insoluble yellow precipitate was filtered, washed with acetic acid and dried in vacuo (0.1 mm Hg) at 60° C. to give 18.5 g (69%) of a yellow powder: m.p. 294.5–295.5° C.

Step 4: Preparation of 6-(4-fluorophenyl)-2-methoxy-5-[4-(methylsulfonyl)phenyl]-pyridine-3-carbonitrile A mixture of 0.34 g (0.92 mMol) of 1,2-dihydro-6-(4-fluorophenyl)-5-[4-(methylthio)phenyl]-2-oxo-pyridine-3-carbonitrile (Step 3) in 10 ml of DMF and 0.33 g of $K_2CO_3$ and 2 ml of iodomethane, was stirred at room temperature over the weekend. The reaction mixture was diluted with 75 ml of water and extracted with dichloromethane (4×25 ml). The combined organic layers were extracted once with 50 ml of 10% NaOH solution then once with brine, dried over $MgSO_4$ and evaporated to dryness. The residue was purified by HPLC to give two fractions. The first fraction was the desired product: m.p. 202.5–204° C.

EXAMPLE 3

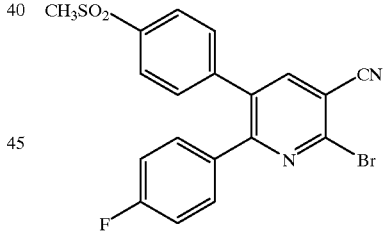

2-Bromo-6-(4-fluorophenyl)-5-[4-(methylsulfonyl)phenyl]-pyridine-3-carbonitrile

A mixture of 1,2-dihydro-6-(4-fluorophenyl)-5-[4-(methylsulfonyl)phenyl]-2-oxo-pyridine-3-carbonitrile (Example 2, Step 3) (0.66 g, 1.81 mMol), 12 ml of 1,2,4-trimethylbenzene, 1.0 g of KBr, and 5 g of $PBr_5$ was heated to 80° C. for 2 hours and then to 180° C. overnight. The reaction mixture was cooled to room temperature and stirred with 75 ml of water for 1 hour. The organic portion was extracted into dichloromethane. The dichloromethane extract was washed once with brine, dried over $MgSO_4$, and evaporated to dryness. The residual oil was purified by HPLC to give 0.55 g (72% yield) of solid: m.p. 229.5–231.5° C.

EXAMPLE 4

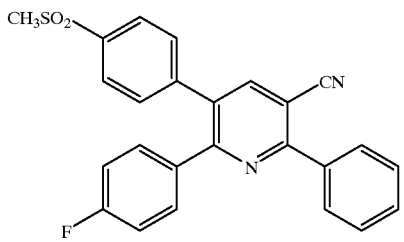

6-(4-Fluorophenyl)-5-[4-(methylsulfonyl)phenyl]-2-phenyl-pyridine-3-carbonitrile To a mixture of 0.1 g (0.23 mmol) of 2-bromo-6-(4-fluorophenyl)-5-[4-(methylsulfonyl)phenyl]-pyridine-3-carbonitrile (Example 3), 10 ml of toluene and 4 ml of ethanol was added 34 mg (0.28 mMol) of phenylboric acid and a solution of 71 mg (0.52 mMol) of $K_2CO_3$ in 1 ml water. To the resulting reaction mixture was added 18 mg of tetrakis(triphenylphosphine)palladium. The mixture was held at reflux overnight, cooled to room temperature, poured into 75 ml of water and extracted with dichloromethane. The combined organic solutions were washed once with 10% NaOH solution, once with brine, dried over $MgSO_4$ and evaporated to dryness to give a yellowish oil which crystallized upon standing. Trituration with ether gave 74.5 mg (76%) of a white powder: m.p. 230–231° C.

EXAMPLE 5

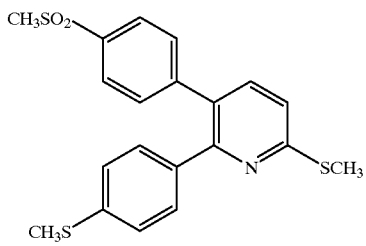

5-[4-(Methylsulfonyl)phenyl]-2-methylthio-6-[4-(methylthio)phenyl]pyridine

To a solution of 2-chloro-6-(4-fluorophenyl)-5-[4-(methylsulfonyl)phenyl]pyridine (Example 1) (296 mg, 0.818 mMol) in 4 ml of dry dimethylformamide was added 172 mg (2.45 mmol) of sodium thiomethoxide. The mixture was stirred at 80° C. overnight. An additional 115 mg (1.64 mMol) of sodium thiomethoxide was added, and stirring continued at 100° C. for 3 hours. After cooling, the mixture was partitioned between ethyl acetate and water, the aqueous layer further extracted twice with dichloromethane, the combined organic extracts dried over sodium sulfate, filtered, and evaporated. Chromatography of the residue over silica gel using 40% ethyl acetate/hexane gave 5-[4-(methylsulfonyl)phenyl]-2-methylthio-6-[4-(methylthio) phenyl]pyridine (172 mg) as a pure white crystalline solid: m.p. 175° C. (DSC). Anal. Calc'd for $C_{20}H_{19}NO_2S_3 \cdot \frac{1}{4} H_2O$ (MW 406.07): C, 59.16; H, 4.72; N, 3.42. Found: C, 59.05; H, 4.78; N, 3.39.

EXAMPLE 6

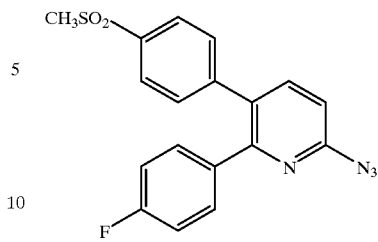

2-Azido-6-(4-fluorophenyl)-5-[4-(methylsulfonyl)phenyl]pyridine

A solution of 1.00 g (2.76 mMol) of 2-chloro-6-(4-fluorophenyl)-5-[4-(methylsulfonyl)phenyl]pyridine (Example 1) and 539 mg (8.29 mMol) of sodium azide in 15 ml of dimethylformamide was stirred in an oil bath at 100° C. for two days. After cooling, the mixture was partitioned between dichloromethane and water. The aqueous layer was further extracted with dichloromethane, the combined organic extracts were dried over sodium sulfate, filtered, and evaporated. Chromatography of the residue over silica gel using ethyl acetate as eluent gave the title compound (376 mg) as a pale yellow crystalline solid: m.p. 229° C. (DSC). Anal. Calc'd for $C_{18}H_{13}N_4O_2S \cdot \frac{1}{4} H_2O$ (MW 372.89): C, 57.98; H, 3.51; N, 15.03. Found: C, 58.35; H, 3.82; N, 14.70.

EXAMPLE 7

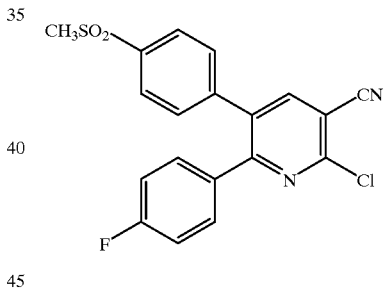

2-Chloro-6-(4-fluorophenyl)-5-[4-(methylsulfonyl)phenyl]-pyridine-3-carbonitrile Step 1: Preparation of 2-chloro-6-(4-fluorophenyl)-5-[4-(methylthio)phenyl]-pyridine-3-carbonitrile A solution of 6-(4-fluorophenyl)-1,2-dihydro-5-[4-(methylthio)phenyl]-2-oxo-pyridine-3-carbonitrile (Example 1, Step 5) (3.7 g, 0.011 mole) in phosphorus oxychloride (45 ml) was stirred at 100° C. for 20 hours. After evaporation of the phosphorus oxychloride the residue was purified by silica gel chromatography and recrystallized from ethyl acetate-hexane.

Step 2: Preparation of 2-chloro-6-(4-fluorophenyl)-5-[4-(methylsulfonyl)phenyl]-pyridine-3-carbonitrile 2-Chloro-6-(4-fluorophenyl)-5-[4-(methylthio)phenyl]-pyridine-3-carbonitrile from Step 1 (1.0 g, 2.82 mMol) and hydrogen peroxide (30%) (3 ml) were stirred and heated (65° C.) in acetic acid (40 ml) for 20 hours and then concentrated to a white solid.

EXAMPLE 8

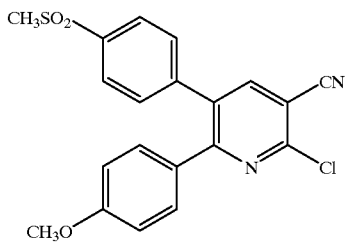

2-Chloro-6-(4-methoxyphenyl)-5-[4-(methylsulfonyl)phenyl]-pyridine-3-carbonitrile Step 1: Preparation of 6-(4-methoxyphenyl)-1,2-dihydro-5-[4-(methylthio)phenyl]2-oxo-pyridine-3-carbonitrile The titled material was obtained as a by-product from the method of Example 1, step 2.

Step 2: Preparation of 2-chloro-6-(4-methoxyphenyl)-5-[4-(methylthio)phenyl]pyridine-3-carbonitrile By the method of Example 7, Step 1 and substituting the product of Step 1 for 6-(4-fluorophenyl)-1,2-dihydro-5-[4-(methylthio)phenyl]-2- oxo-pyridine-3-carbonitrile, 2-chloro-6-(4-methoxyphenyl)-5-[4-(methylthio)phenyl] pyridine-3-carbonitrile was obtained as a solid: m.p. (DSC): 165.66° C. Anal. Calc'd. for $C_{20}H_{15}N_2OSCl$ (366.87): C, 65.48; H, 4.12; N, 7.64. Found: C, 65.37; H, 3.99; N, 7.55.

Step 3: Preparation of 2-chloro-6-(4-methoxyphenyl)-5-[4-(methylsulfonyl)phenyl]pyridine-3-carbonitrile 2-Chloro-6-(4-methoxyphenyl)-5-[4-(methylthio)phenyl] pyridine-3-carbonitrile from Step 2 (100 mg, 0.27 mMol) and hydrogen peroxide (30%) (1 ml) in acetic acid were stirred at room temperature for 3 days and concentrated to a white solid. The product was purified by silica gel chromatography. Anal. Calc'd. for $C_{22}H_{19}N_2O_3SF$: C, 64.38; H, 4.67; N, 6.82. Found: C, 64.12; H, 4.82; N, 6.72.

EXAMPLE 9

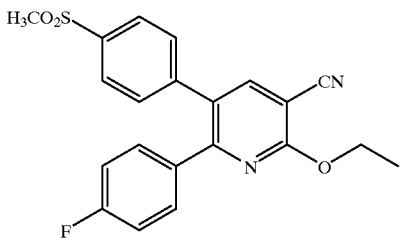

2-Ethoxy-6-(4-fluorophenyl)-5-[4-(methylsulfonyl) phenyl]-pyridine-3-carbonitrile 2-Chloro-6-(4-fluorophenyl-5-[4-(methylsulfonyl) phenyl]pyridine-3-carbonitrile (Example 7) (200 mg, 0.52 mMol) was added to freshly prepared sodium ethoxide (0.57 mMol) (from addition of sodium metal to ethyl alcohol) in ethyl alcohol (50 ml) and heated to 65° C. for 3.5 hours. The reaction mixture was cooled to room temperature. Water (3 ml) was added and the mixture was concentrated. The product was partitioned between water (50 ml) and ethyl acetate (50 ml). The ethyl acetate portion was dried over sodium sulfate, filtered and concentrated to a solid. The product was purified by a silica gel chromatography to give a white solid: m.p. (DSC): 207.22° C. Anal. Calc'd. for $C_{21}H_{17}N_2O_3SF$ (396.44): C, 63.62; H, 4.32; N, 7.07. Found: C, 63.56; H, 4.32; N, 6.88.

EXAMPLE 10

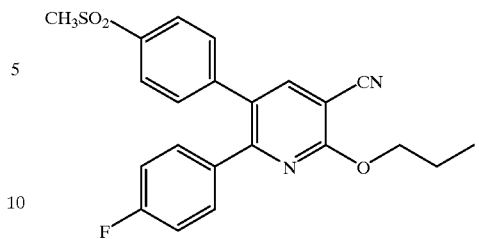

6-(4-Fluorophenyl)-5-[4-(methylsulfonyl)phenyl]-2-propoxypyridine-3-carbonitrile The titled compound was prepared by the method of Example 9 and by the substitution of sodium in propyl alcohol for sodium in ethyl alcohol. The product was purified by silica gel chromatography to give a solid. Anal. Calc'd. for $C_{22}H_{19}N_2O_3SF$: C, 64.38; H, 4.67; N, 6.82. Found: C, 64.12; H, 4.82; N, 6.72.

EXAMPLE 11

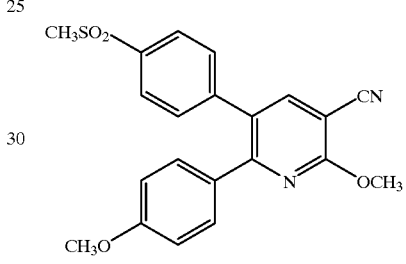

2-Methoxy-6-(4-methoxyphenyl)-5-[4-(methylsulfonyl)phenyl]pyridine-3-carbonitrile 2-Chloro-6-(4-methoxyphenyl)-5-[4-(methylsulfonyl) phenyl]pyridine-3-carbonitrile (Example 8) (100 mg, 0.25 mMol) was added to freshly prepared sodium methoxide (0.27 mMol) in methanol and stirred at room temperature for 22 hours and then at 75° C. for 4 hours. The reaction solution was concentrated and the product was purified by silica gel chromatography to give a white solid. Anal. Calc'd. for $C_{21}H_{18}N_2O_4S$ (394.45): C, 63.95; H, 4.60; N, 7.10. Found: C, 63.80; H, 4.71; N, 6.94.

EXAMPLE 12

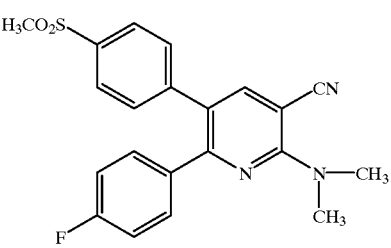

2-(Dimethylamino)-6-(4-fluorophenyl)-5-[4-(methylsulfonyl)phenyl]pyridine-3-carbonitrile 2-Chloro-6-(4-fluorophenyl)-5-[4-(methylsulfonyl) phenyl]pyridine-3-carbonitrile (Example 7) (200 mg, 0.52 mMol) in ethanol (150 ml) was charged with dimethylamine. The solution was shaken for 24 hours at 70° C. and a pressure of 22 psi in a Parr shaker. The solution was concentrated. The residue was titurated with methyl alcohol and filtered to give a yellow solid: m.p. (DSC) : 205.02° C. Anal. Calc'd. for $C_{21}H_{18}N_3O_2SF$ (395.46): C, 63.78; H, 4.59; N, 10.63. Found: C, 64.02; H, 4.58; N, 10.77.

EXAMPLE 13

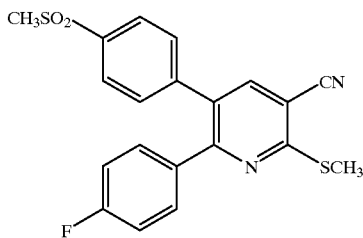

6-(4-Fluorophenyl)-5-[4-(methylsulfonyl)phenyl]-2-(methylthio)pyridine-3-carbonitrile By the method of Example 9 and substituting sodium thiomethoxide for sodium ethoxide, the title compound was obtained as a white solid mp (DSC): 204.40° C. Anal. Calc'd. for $C_{20}H_{15}N_2O_2S_2F$ (398.48): C, 60.28; H, 3.79; N, 7.03. Found: C, 60.40; H, 3.79; N, 7.02.

EXAMPLE 14

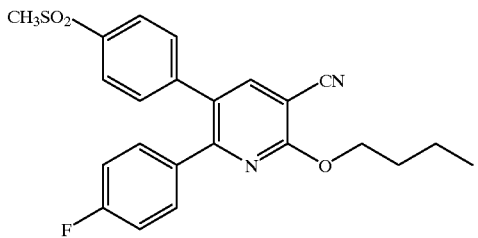

2-Butoxy-6-(4-fluorophenyl)-5-[4-(methylsulfonyl)phenyl]pyridine-3-carbonitrile

The titled compound was prepared by the method of Example 9 with the substitution of sodium in butyl alcohol for sodium in ethanol. Anal. Calc'd. for $C_{23}H_{21}N_2O_3SF$ (424.50): C, 65.08; H, 4.99; N, 6.60. Found: C, 64.95; H, 4.82; N, 6.39.

EXAMPLE 15

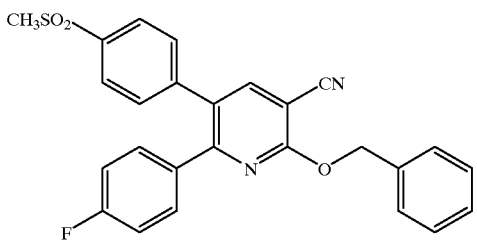

6-(4-Fluorophenyl)-5-[4-(methylsulfonyl)phenyl]-2-(phenylmethoxy)pyridine-3-carbonitrile 6-(4-Fluorophenyl)-1,2-dihydro-5-[4-(methylsulfonyl)phenyl]-2-oxo-pyridine-3-carbonitrile (Example 1, Step 6) (200 mg, 0.54 mMol), silver carbonate (150 mg, 0.54 mMol) and benzyl chloride (1 ml) were stirred in acetone (100 ml) and dimethylformamide (25 ml) at room temperature for 48 hours. The mixture was filtered and the filtrate was concentrated to a white solid which was recrystallized from chloroform-methanol: m.p. (DSC): 204.81° C. Anal. Calc'd. for $C_{26}H_{19}N_2O_3SF$ (458.52): C, 68.11; H, 4.18; N, 6.11. Found: C, 67.81; H, 4.16; N, 6.04.

EXAMPLE 16

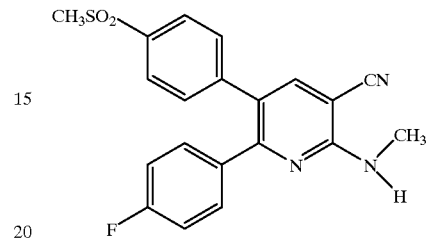

6-(4-Fluorophenyl)-2-(methylamino)-5-[4-(methylsulfonyl)phenyl]pyridine-3-carbonitrile 2-Chloro-6-(4-fluorophenyl)-5-[4-(methylsulfonyl)phenyl]pyridine-3-carbonitrile (Example 7) (200 mg, 0.52 mMol) was charged with methylamine. The solution was shaken for 24 hours at 70° C. and 74 psi by a Parr Shaker. The vessel was cooled to room temperature and vented to allow excess methylamine to evaporate leaving a yellow solid. The solid was washed with methyl alcohol and recrystallized from chloroform: m.p. (DSC): 295.63° C. Anal. Calc'd. for $C_{20}H_{16}N_3O_2SF$ (381.43): C, 62.98; H, 4.23; N, 11.02. Found: C, 62.59; H, 4.15; N. 10.77.

EXAMPLE 17

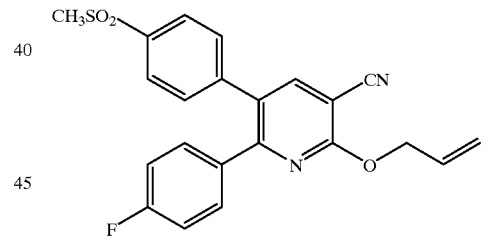

6-(4-Fluorophenyl)-5-[4-(methylsulfonyl)phenyl]-2-[(2-propenyl)oxy]pyridine-3-carbonitrile Step 1: Preparation of 6-(4-fluorophenyl)-5-[4-(methylthio)phenyl]-2-[(2-propenyl)oxy]pyridine-3-carbonitrile 6-(4-Fluorophenyl)-1,2-dihydro-5-[4-(methylthio)phenyl]-2-oxo-pyridine-3-carbonitrile (Example 1, Step 5) (100 mg, 0.297 mMol), silver carbonate (82 mg, 0.297 mMol) and allyl chloride were stirred in a brown vessel in acetone (25 ml) for 48 hours. The reaction mixture was filtered. The filtrate was condensed to give the crude compound as a solid. 6-(4-Fluorophenyl)-5-[4-(methylthio)phenyl]-2-[(2-propenyl)oxy]-pyridine-3-carbonitrile was purified by silica gel chromatography and recrystallized from hexane. Anal. Calc'd. for $C_{22}H_{17}N_2OSF$: C, 70.19; H, 4.55; N, 7.44. Found: C, 69.80; H, 4.60; N, 7.32.

Step 2: Preparation of 6-(4-fluorophenyl)-5-[4-(methylsulfonyl)phenyl]-2-[(2-propenyl)oxy[pyridine-3-carbonitrile 6-(4-Fluorophenyl)-5-[4-(methylthio)phenyl]-2-[(2-propenyl)oxy]pyridine-3-carbonitrile from Step 1 (81 mg, 0.2 mMol) was stirred at room temperature in acetic acid (4 ml) with aqueous hydrogen peroxide (30%, 1 ml) for 24 hours. The solution was concentrated. The residue was dissolved in ethyl acetate, filtered and concentrated to a white solid which was recrystallized from ethyl acetate. Anal. Calc'd. for $C_{22}H_{17}N_2O_3SF$ (408.45): C, 64.69; H, 4.20; N, 6.86. Found: C, 64.35; H, 4.12; N, 6.58.

EXAMPLE 18

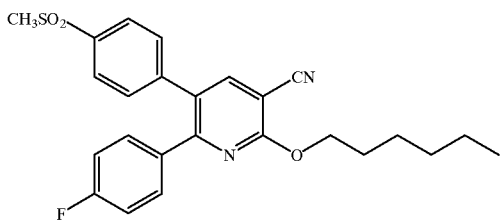

6-(4-Fluorophenyl)-2-hexyloxy-5-[4-(methylsulfonyl)phenyl]pyridine-3-carbonitrile The titled compound was prepared by the method of Example 9 with the substitution of sodium in hexyl alcohol for sodium in ethanol. The product was recrystallized from ethyl acetate-hexane as a white solid: Anal. Calc'd. for $C_{25}H_{25}N_2O_3SF$ (452.55): C, 66.35; H, 5.57; N, 6.19. Found: C, 66.44; H, 5.83; H, 6.07.

EXAMPLE 19

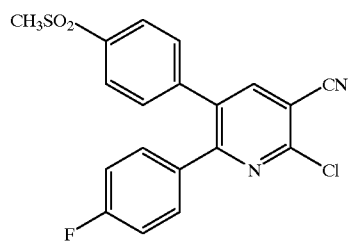

2-Chloro-6-(4-fluorophenyl)-5-[4-(methylsulfonyl)phenyl]pyridine-3-carbonitrile

In an alternative preparation of Example 7, to a Parr reactor was charged 5 g (13.6 mMol) of 1,2-dihydro-6-(4-fluorophenyl)-5-[4-(methylthio)phenyl]-2-oxo-pyridine-3-carbonitrile (Example 1, Step 2) and 10 ml of $POCl_3$. The reaction mixture was heated in oil bath overnight at 190° C. and cooled to room temperature. The semi-solid reaction mixture was added slowly to 600 ml of water. The mixture was stirred and a grayish insoluble precipitate was filtered and air dried to recover 5.7 g of solid. Recrystallization from 500 ml boiling methanol gave 1.7 g (32%) of light brown crystals.

EXAMPLE 20

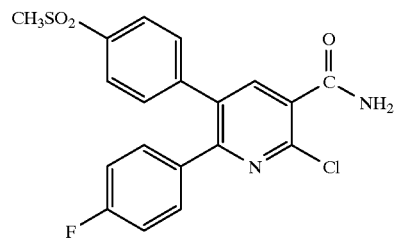

2-Chloro-6-(4-fluorophenyl)-5-[4-(methylsulfonyl)phenyl]pyridine-3-carboxamide

To 0.13 g (0.34 mMol) of 6-(4-fluorophenyl)-2-methoxy-5-[4-(methylsulfonyl)phenyl]pyridine-3-carbonitrile (Example 19) was added 9 g of conc. $H_2SO_4$. The mixture was stirred at room temperature over the weekend and was poured into 75 ml of water. An insoluble white precipitate was formed which filtered, washed with water and dried in vacuo (0.1 mm Hg) at 50° C. to give 69.5 mg of a white powder. Recrystallization from ethyl acetate/hexane yielded 48.8 mg (35%) of a solid: m.p. 240° C.

EXAMPLE 21

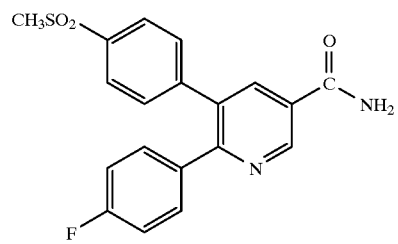

6-(4-Fluorophenyl)-5-[4-(methylsulfonyl)phenyl]pyridine-3-carboxamide

To 0.13 g (0.32 mMol) of the product of Example 20 in a 6 oz. Fisher/Porter vessel with a magnetic stirrer was added 100 ml of dichloromethane and 0.6 ml of triethylamine followed by 0.1 g of 10% Pd on carbon catalyst. This mixture was hydrogenated for 2 hours at 70 psi and filtered. The filtrate was washed with water then brine, dried over $MgSO_4$ and evaporated to dryness to give 0.13 g of a yellowish solid. Trituration with ether recovered 95.4 mg of a faintly yellow product.

EXAMPLE 22

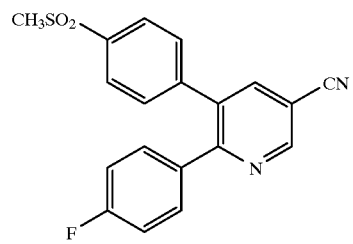

6-(4-Fluorophenyl)-5-[4-(methylsulfonyl)phenyl]pyridine-3-carbonitrile

A mixture of 75 mg (0.20 mMol) of the product of Example 21 and 5 ml of $POCl_3$ was heated to 100° C. for 2 hours, cooled to room temperature, poured into ice-water and extracted with dichloromethane (4×15 ml). The combined organic layers were extracted once with brine, dried over MgSO₄ and evaporated to dryness to recover a colorless oil. Trituration with ether gave a colorless solid which was dried at 0.1 mm Hg at 50° C. to give 29.9 mg (42%) of solid: m.p. 178–181.5° C.

EXAMPLE 23

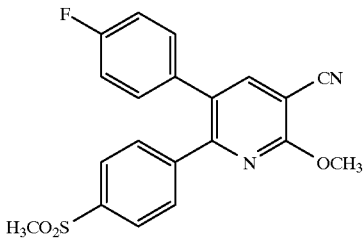

6-(4-Fluorophenyl)-2-methoxy-5-[4-(methylsulfonyl)phenyl]pyridine-3-carbonitrile The titled compound was prepared by the method of Example 4 from 2-(4-fluorophenyl)-1-(4-(methylthio) phenyl)ethanone as made in U.S. Pat. No. 3,647,858, Example 1, to give a white solid: Mass spectrum (M⁺)=382.

EXAMPLE 24

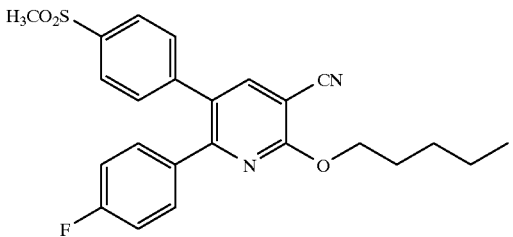

6-(4-Fluorophenyl)-5-[4-(methylsulfonyl)phenyl]-2-pentoxypyridine-3-carbonitrile The titled compound was prepared by the method of Example 9 and by the substitution of sodium in pentyl alcohol for sodium in ethyl alcohol. The product was purified by recrystallization from ethyl acetate-hexane: mp (DSC): 153.62° C. Anal. Calc'd. $C_{24}H_{23}N_2O_3SF$: C, 65.74; H, 5.29; N, 6.39. Found: C, 65.67; H, 5.40; N, 6.25.

EXAMPLE 25

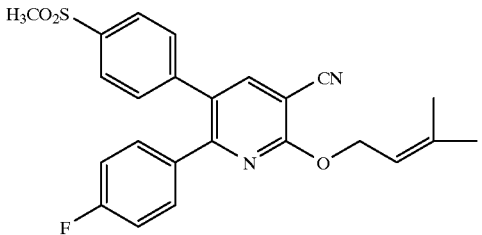

6-(4-Fluorophenyl)-5-[4-(methylsulfonyl)phenyl]-2-(2-methyl-2-butenyloxy)pyridine-3-carbonitrile The titled compound was obtained by following the method of Example 2 and by the substitution of 4-bromo-2-methyl-2-butene for iodomethane: mp (DSC): 149.21° C. Anal. Calc'd. $C_{24}H_{21}N_2O_3SF$: C, 66.04; H, 4.85; N, 6.42. Found: C, 65.87; H. 5.11; N, 6.31.

EXAMPLE 26

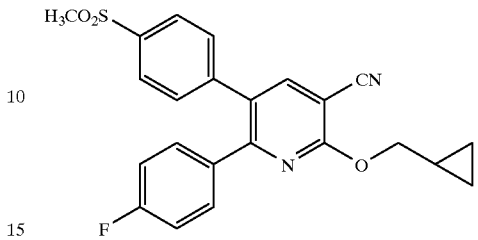

2-Cyclopropylmethoxy-6-(4-fluorophenyl)-5-[4-(methylsulfonyl)phenyl]pyridine-3-carbonitrile The titled compounds were obtained by following the method of Example 2 and by the substitution of bromomethyl cyclopropane for iodomethane. Anal. Calc'd. $C_{23}H_{19}N_2O_3SF \cdot 0.2M\ H_2O$: C, 64.84; H, 4.59; N. 6.57. Found: C, 64.81; H, 4.74; N, 6.48.

EXAMPLE 27

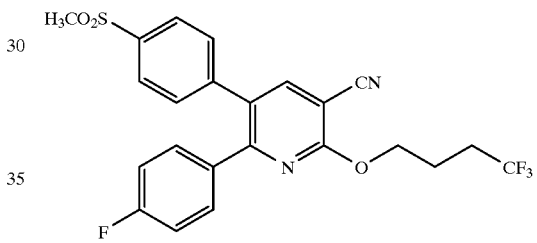

6-(4-Fluorophenyl)-5-[4-(methylsulfonyl)phenyl]-2-(4,4,4-trifluorobutoxy)pyridine-3-carbonitrile The titled compound was obtained by following the method of Example 2 and by the substitution of 4,4,4-trifluoro-1-bromobutane for iodomethane. Anal. Calc'd. for $C_{23}H_{18}N_2O_3SF$: C, 57.74; H, 3.79; N, 5.85. Found: C, 57.65; H, 3.99; N, 5.78.

EXAMPLE 28

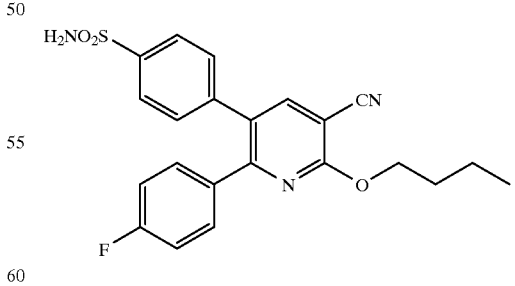

4-[6-butoxy-4-cyano-2-(4-Fluorophenyl)-3-pyridine] benzenesulfonamide

To a solution of 2-butoxy-6-(4-fluorophenyl)-5-(4-(methylsulfonyl)phenyl]pyridine-3-carbonitrile (Example 14) (2.12 gm, 0.005 mole.) in dry tetrahydrofuran (800 ml)

cooled with an ice bath to 0° C. was added n-butylmagnesium chloride (2.0M in tetrahydrofuran, 12.5 mL, 0.025 mole) by a syringe over 10 minutes. The ice bath was removed and the solution was allowed to stir at room temperature for 2.5 hours. After re-cooling to 0° C. with an ice bath triethylborane (1.0M in tetrahydrofuran, 30 mL, 0.030 mole) was added by syringe over 5 minutes. The solution was heated to reflux for 2.5 hours. After cooling to room temperature, a solution of sodium acetate (10.5 gm) and hydroxylamine-O-sulfonic acid (10.5 gm) in water (75 mL) was added with stirring. After 1.5 hours the two layers were separated. The organic layer was concentrated and the residue dissolved in ethyl acetate. The previous water layer was washed with ethyl acetate. The two ethyl acetate solutions were combined, dried over anhydrous sodium sulfate, filtered and concentrated to a yellow oil. The product was purified by silica gel chromatography. Anal. Calc'd. $C_{22}H_{20}N_3O_3SF$: C, 62.10; H. 4.74; N, 9.88. Found: C, 62.36; H, 4.87; N, 9.67.

EXAMPLE 29

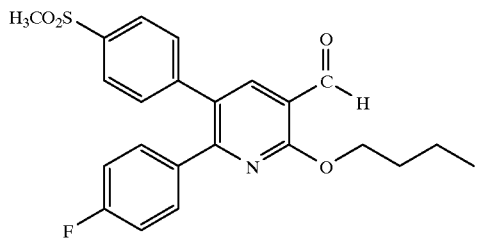

2-Butoxy-6-(4-fluorophenyl)-5-[4-(methylsulfonyl) phenyl]pyridine-3-methanol

EXAMPLE 30

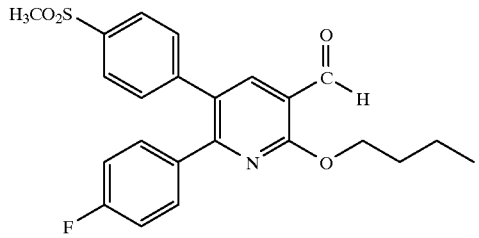

2-Butoxy-6-(4-fluorophenyl)-5-[4-(methylsulfonyl) phenyl]pyridine-3-carboxaldehyde Diisobutyl aluminum hydride (1.0M in toluene, 3 mL, 3 mMol) was added in three portions over 26 hours (0 hours, 24 hours, 26 hours) to a solution of 2-butoxy-6-(4-fluorophenyl)-5-[4-(methylsulfonyl)phenyl]pyridine-3-carbonitrile, Example 14, (0.42 gm, 1 mMol) in toluene (75 mL) and stirred at room temperature. Methyl alcohol (5 mL) was added dropwise followed by a solution of water (5 mL) in methyl alcohol (25 mL). The layers were separated and the organic layer was dried over anhydrous sodium sulfate, filtered and concentrated to a semi-solid. The products were separated and purified by silica gel chromatography. Example 29 Anal. Calc'd. $C_{23}H_{24}NO_4SF$: C, 64.32; H, 5.63; N, 3.26. Found: C, 64.27; H, 5.59; N, 3.23. Example 30 Anal. Calc'd. $C_{23}H_{22}NO_4SF$: C, 64.62; H, 5.19; N, 3.28. Found: C, 64.84; H, 5.39; N, 3.58.

EXAMPLE 31

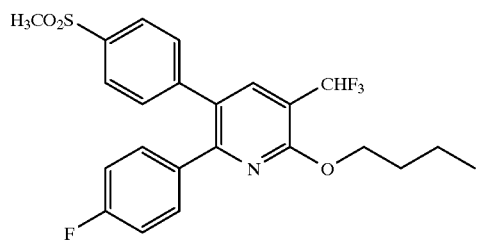

2-Butoxy-3-difluoromethyl-6-(4-fluorophenyl)-5-[4-(methylsulfonyl)phenyl]pyridine Diethylamino sulfur trifluoride (0.135 gm, 0.00084 mole) was added to a stirring solution of 2-butoxy-6-(4-flourophenyl)-5-[4-(methylsulfonyl)phenyl]-3-pyridinecarboxaldehyde (Example 30) (0.12 gm, 0.00028 mole) in methylene chloride (50 mL) and stirred at room temperature for 24 hours. The solution was concentrated. The 5 titled material was purified by silica gel chromatography. The structure was supported by mass spectroscopy. Anal. Calc'd. $C_{23}H_{22}NO_3SF_3$: C, 61.46; H, 4.93; N. 3.12. Found: C, 61.85; H, 5.27; N, 2.96.

EXAMPLE 32

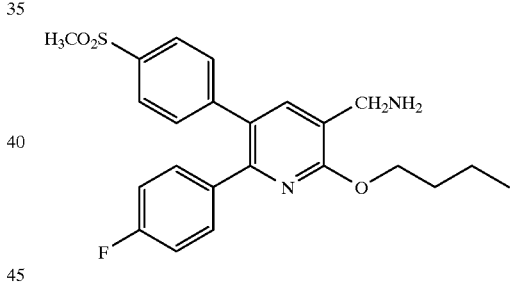

2-Butoxy-6-(4-fluorophenyl)-5-[4-(methylsulfonyl) phenyl]pyridine-3-methylamine

Borane-tetrahydrofuran (1.0M in tetrahydrofuran, 1.5 mL, 0.0016 mole) was added by syringe to a solution of 2-butoxy-6-(4-fluorophenyl)-5-[4-(methylsulfonyl)phenyl] pyridine-3-carbonitrile (Example 14) (0.68 g, 0.0016 mole) in tetrahydrofuran (100 mL). After stirring at room temperature for 1 hour the solution was heated to reflux for 20 hours. Additional borane-tetrahydrofuran (2.4 mL) was added in three portions over the next 3 hours to the hot solution and stirred for 1 hour before cooling to room temperature. Methanol (20 mL) was added and the solution was concentrated to an oily solid. The product was purified by silica gel chromatography (Example 29) (128 mg, 0.3 mMol) in dimethylformamide after hydroxymethyl-5-[4-(methylsulfonyl)phenyl]pyridine.

EXAMPLE 33

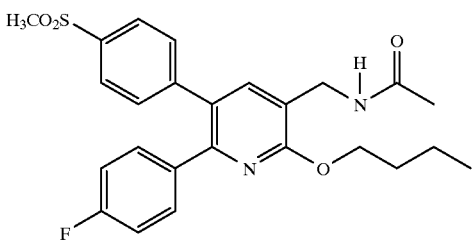

2-Butoxy-6-(4-fluorophenyl)-3-(N-methylcarbonylamino)methyl-5-[4-(methylsulfonyl)phenyl3pyridine Acetyl chloride (several drops) was added to Example 32 (50 mg) in tetrahydrofuran (10 mL) and stirred for 24 hours at room temperature. The reaction was concentrated to an oily solid. The product was purified by silica gel chromatography. Anal. Calcd. $C_{25}H_{27}N_2O_4SF$: C, 63.81; H, 5.78; N, 5.95. Found: C, 63.59; H, 5.97; N, 5.80.

EXAMPLE 34

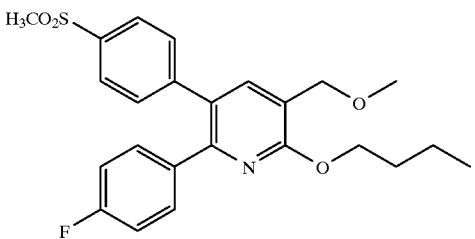

2-Butoxy-6-(4-fluorophenyl)-3-(methoxymethyl)-5-[4-(methylsulfonyl)phenyl]pyridine Sodium hydride (11 mg 4.5 mMol) is added to a stirring solution of 2-butoxy-6-(4-fluorophenyl)-3-hydroxymethyl-5-[4-(methylsulfonyl)phenyl]pyridine (50 mL). After 1 hour, methyl iodide (85 mg, 0.6 mMol) is added and the reaction mixture is stirred for 20 hours at room temperature. Water (1 mL) is added dropwise and the mixture is concentrated to an oily solid. The titled material is purified by silica gel chromatography.

EXAMPLE 35

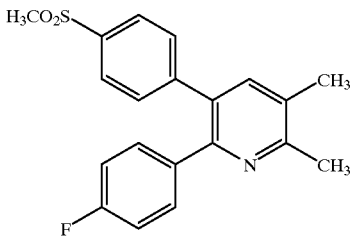

6-(4-Fluorophenyl)-2-methyl-5-[4-(methylsulfonyl)phenyl]pyridine-3-carbonitrile

Step 1 Preparation of 4-fluoro-γ-[4-(methylthio)phenyl]-α-(1-oxoethyl)-δ-oxobenzeneletanenitrile A solution of 1-(N,N-dimethylamino)-3-(4-fluorophenyl)-2-[4-(methylthio)phenyl]prop-1-en-3-one (Example 2, Step 1) (13 gm, 0.041 mole) and 3-oxo-propyl cyanide [J.C. Krauss, et al, *Synthesis*, 308–309, (1983)] (3.4 gm, 0.041 mole) in dimethylformamide (10 mL) containing methyl alcohol (4 mL) is added dropwise to a cold (0° C.) slurry of sodium hydride (2 g) in dimethylformamide (50 mL). The mixture is heated to 80° C. for 4 hours. The mixture is cooled to room temperature and poured into 1M sodium phosphate, monobasic (500 mL). The material is filtered, washed with water and air dried.

Step 2: Preparation of 6-(4-fluorophenyl)-2-methyl-5-[4-(methylthio)phenyl]pyridine-3-carbonitrile 4-Fluoro-γ-[4-(methylthio)phenyl]-α-(1-oxoethyl)-δ-oxobenzenepetanenitrile from Step 1, is treated with a solution of tetrahydrofuran saturated with ammonia. The reaction mixture is concentrated and the compound is purified by silica gel chromatography.

Step 3: Preparation of 6-(4-fluorophenyl)-2-methyl-5-[4-(methylsulfonyl)phenyl]pyridine-3-carbonitrile.

By following the procedure of Example 2, Step 3 and by substituting 6-(4-fluorophenyl)-2-methyl-5-(4-(methylthio)phenyl]pyridine-3-carbonitrile from Step 2 above for 1,2-dihydro-6-(4-fluorophenyl)-5-(4-(methylthio)phenyl)-2-oxo-pyridine-3-carbonitrile (Example 2, Step 2] the titled material is prepared.

EXAMPLE 36

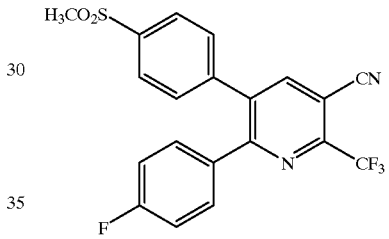

6-(4-Fluorophenyl)-5-[4-(methylsulfonyl)phenyl]-2-trifluoromethylpyridine-3-carbonitrile By the substitution of 4,4,4-trifluoro-3-oxo-propylcyanide for 3-oxo-propylcyanide in Example 35, Step 1 and following the procedures of Example 35, Step 2 and 3 the titled material is prepared.

EXAMPLE 37

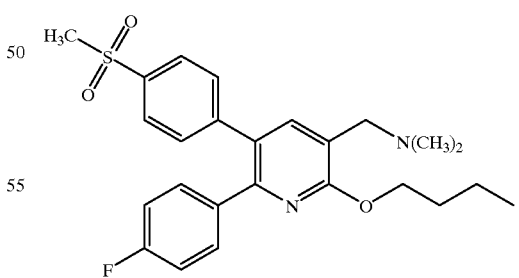

2-Butoxy-6-(4-fluorophenyl)-N,N-dimethyl-5-[4-(methylsulfonyl)phenyl]pyridine-3-methanamine Aqueous 37% formaldehyde (1 ml) was added to a stirring solution of 2-butoxy-6-(4-fluorophenyl)-5-[4-(methylsulfonyl)phenyl]pyridine-3-methylamine [Example 32] (250 mg, 0.58 mmol) in 5 ml acetonitrile. Sodium cyanoborohydride (54 mg, 0.875 mmol) was added and the reaction mixture was stirred for 15 minutes. Two drops of acetic acid was added and the reaction mixture was stirred for 2 hours. The reaction mixture was concentrated to a paste and the titled material was purified by silica gel chromatography. Anal Calc'd. $C_{25}H_{29}N_2O_3SF+0.25\ H_2O$: C, 65.12; H, 6.45; N, 6.08. Found: C, 65.12; H, 6.46; N, 6.19.

EXAMPLE 38

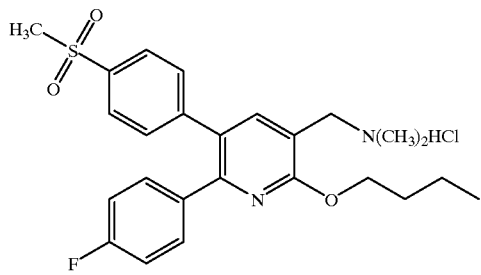

2-Butoxy-6-(4-fluorophenyl)-N,N-dimethyl-5-[4-(methylsulfonyl)phenyl]pyridine-3-methanamine hydrochloride Acetyl chloride (10 drops) was added to a stirring solution of 2-butoxy-6-(4-fluorophenyl)-5-[4-(methylsulfonyl)phenyl]pyridine-3-dimethylamine [Example 37] (60 mg) in 50 mL diethyl ether containing 1 ml methyl alcohol. After 1 hour, a white solid was filtered off and washed with diethyl ether to yield the hydrochloride salt: mp. (DSC): 251.64° C. Anal. Calc'd. $C_{25}H_{30}N_2O_3SFCl+0.1\ m\ H_2O$: C, 60.68; H, 6.15; N, 5.66. Found: C, 60.36; H, 6.24; N, 5.59.

EXAMPLE 39

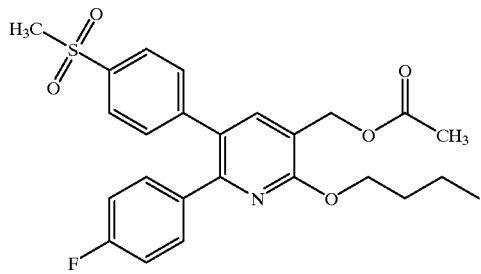

2-Butoxy-6-(4-fluorophenyl)-5-[4-(methylsulfonyl)phenyl]pyridine-3-methanol, acetate Acetyl chloride (28 mg, 0.35 mMol) was added to a stirring solution of 2-butoxy-6-(4-fluorophenyl)-5-[4-(methylsulfonyl)phenyl]pyridine-3-methanol [Example 29] (100 mg, 0.23 mMol) in 50 ml tetrahydrofuran (THF). After stirring at room temperature for 20 hours, 2 drops of acetylchloride were added and the mixture was warmed to 50° C. After 24 hours, 2 more drops of acetyl chloride were added. This process was repeated after 24 hours. The reaction solution was stirred at room temperature for 20 hours and concentrated to an oil. Silica gel chromatography yielded the titled material. Anal. Calcd. $C_{25}H_{26}NO_5SF+0.5\ H_2O$: C, 62.49; H. 5.66; N, 2.91. Found: C, 62.58; H, 5.92; N, 2.81.

EXAMPLE 40

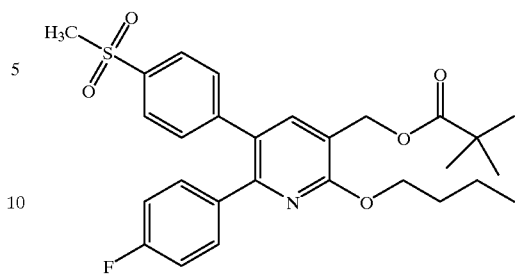

[2-Butoxy-6-(4-fluorophenyl)-5-[4-(methylsulfonyl)phenyl]pyridin-3-yl]methylbutanoate The titled material was prepared by the method of Example 39 by the substitution of butyryl chloride for acetyl chloride. Anal. Calc'd. $C_{27}H_{30}NO_5SF$: C, 64.91; H, 6.05; N, 2.80. Found: C, 64.87; H, 5.98; N, 2.71.

EXAMPLE 41

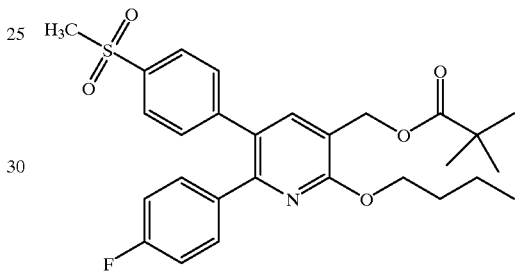

[2-Butoxy-6-(4-fluorophenyl)-5-[4-(methylsulfonyl)phenyl]pyridin-3-yl]methyl-2,2-propanoate Pyridine (4 drops) was added to a stirring solution of 2-butoxy-6-(4-fluorophenyl)-5-[4-(methylsulfonyl)phenyl]pyridine-3-methanol [Example 29] (100 mg, 0.23 mMol) and trimethylacetyl chloride (42 mg, 0.35 mMol) in 50 ml THF and stirred for 20 hours. After warming the reaction solution to 55° C. for 4 hours, the solution was concentrated to an oil. The titled material was purified by silica gel chromatography. Anal. Calc'd. $C_{28}H_{32}NO_5SF+0.25\ H_2O$: C, 64.91; H, 6.32; N, 2.70. Found: C, 64.84; H, 6.12; N, 2.82.

EXAMPLE 42

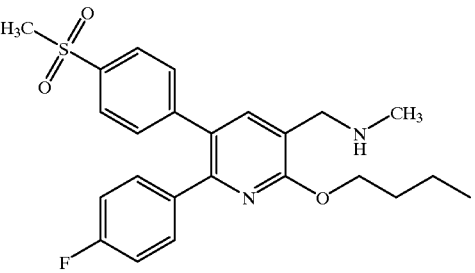

2-Butoxy-6-(4-fluorophenyl)-N-methyl-5-[4-(methylsulfonyl)phenyl]pyridine-3-methanamine Methylamine (2.0M in methanol, 1 ml) was added to a stirring mixture of 2-butoxy-6-(4-fluorophenyl)-5-[4-

(methylsulfonyl)phenyl]pyridine-3-carboxaldehyde [Example 30] (150 mg, 0.35 mMol) and molecular sieves (3A, 1.0 g) in 50 ml methanol. After stirring for 4 hours, the mixture was cooled by an ice bath and 5 ml 5% HCl was added. The mixture was concentrated to an oil containing the molecular sieves. Water (50 ml) and 5 ml 5% NaHCO$_3$ were added and the product was extracted into ethyl acetate (2×50 ml). The ethyl acetate extracts were combined, dried over Na$_2$SO$_4$, filtered and concentrated to a solid. The titled material was purified by silica gel chromatography to give a solid: m.p. (DSC) 113.98° C. Anal. Calc'd. C$_{24}$H$_{27}$N$_2$O$_3$SF: C, 65.14; H. 6.15; N, 6.33. Found: C, 64.81; H, 6.15; N, 6.17.

EXAMPLE 43

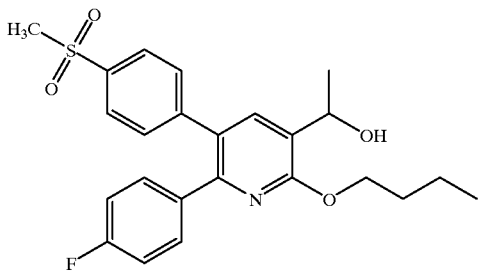

(+/−) 2-Butoxy-6-(4-fluorophenyl)-α-methyl-5-[4-(methylsulfonyl)phenyl]pyridine-3-methanol Methyl lithium (0.67 ml, 1.5M in diethyl ether, 1.02 mMol) was added by syringe to a stirring solution of 2-butoxy-6-(4-fluorophenyl)-5-[4-(methylsulfonyl)phenyl] pyridine-3-carboxaldehyde [Example 30](0.38 g, 0.88 mMol) in 50 mL THF cooled to −75° C. The cold bath was removed and the reaction mixture was allowed to come to room temperature. Acetic acid (10%, 5 ml) was added. After stirring for 30 minutes, the layers were separated. The organic layer was washed with 50 ml water, dried over sodium sulfate, filtered and concentrated to an oil. The titled material was purified by silica gel chromatography and recrystallized from ethyl acetate-hexane. Anal. Calc'd. C$_{24}$H$_{26}$NO$_4$SF; C, 64.99; H, 5.91; N, 3.16. Found: C, 64.96; H, 6.07; N, 3.07.

EXAMPLE 44

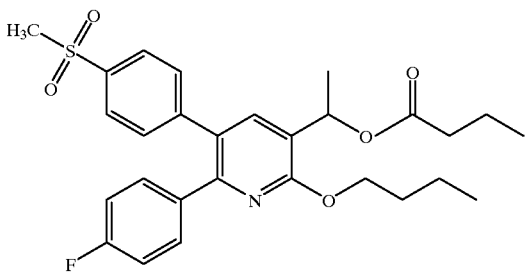

(+/−) 1-[2-Butoxy-6-(4-fluorophenyl)-5-[4-(methylsulfonyl)phenyl]pyridin-3-yl]ethylbutanoate The titled material was prepared by the method of Example 41 with the substitution of the product of [Example 43] for 2-butoxy-6-(4-fluorophenyl)-5-[4-(methylsulfonyl) phenyl]pyridine-3-methanol [Example 29]. Anal. Calc'd.

C$_{28}$H$_{32}$NO$_5$SF+0.75 H$_2$O: C, 63.80; H, 6.41; N, 2.66. Found: C, 63.65; H, 6.27; N, 2.53.

Biological Evaluation

Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testinc NSAIDs* in *Non-steroidal Anti-Inflammatory Drugs*, (J. Lombardino, ed. 1985)). The % inhibition shows the % decrease from control paw volume determined in this procedure and the data for selected compounds in this invention are summarized in Table I.

TABLE I

| RAT PAW EDEMA | |
|---|---|
| Example | % Inhibition @ 10 mg/kg body weight |
| 2 | 16 |
| 3 | 16 |
| 4 | 18 |

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of Recombinant COX Baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2×10$^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10$^7$–10$^8$ pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX-1 and COX-2 activity COX activity was assayed as PGE2 formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II

| Example | COX-2 $ID_{50}$ μM | COX-1 $ID_{50}$ μM | SPECIES human (h)/murine (m) |
|---|---|---|---|
| 1  | 29    | >100 | h |
| 2  | 0.2   | >100 | h |
| 3  | <0.1  | >10  | m |
| 4  | <0.1  | >10  | m |
| 5  | <0.1  | >100 | h |
| 6  | 2.0   | >100 | h |
| 7  | 0.1   | >100 | m |
| 10 | 0.2   | >100 | h |
| 11 | 0.4   | >100 | h |
| 12 | 0.6   | >100 | h |
| 13 | 0.2   | >100 | h |
| 14 | <0.1  | >100 | h |
| 15 | <0.1  | >100 | h |
| 16 | 2.3   | >100 | h |
| 17 | <0.1  | >100 | h |
| 18 | 0.2   | >100 | h |
| 20 | 26.2  | >100 | m |
| 21 | 105   | >100 | m |
| 22 | 0.3   | >10  | m |
| 23 | 0.3   | >100 | m |
| 24 | <0.1  | >100 | h |
| 25 | 0.1   | >100 | h |
| 27 | 0.2   | >100 | h |
| 28 | <0.1  | 0.2  | h |
| 29 | <0.1  | >100 | h |
| 31 | <0.1  | >100 | h |
| 32 | 1.6   | >100 | h |
| 33 | 1.4   | >100 | h |
| 37 | 0.8   | >100 | h |
| 39 | 0.1   | >100 | h |
| 40 | 0.1   | >100 | h |
| 41 | >100  | >100 | h |
| 42 | 3.0   | >100 | h |
| 43 | 0.1   | 28   | h |
| 44 | 2.0   | >100 | h |

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients. in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations

What is claimed is:
1. A compound of Formula I

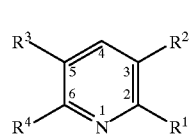

(I)

wherein $R^1$ is selected from hydrido, halo, alkyl, haloalkyl, alkoxy, haloalkoxy, aryl, alkylthio, alkylamino, aralkoxy, aralkylthio, aralkylamino, N-alkyl-N-aralkylamino, heteroaralkoxy, heteroaralkylthio, heteroaralkylamino, N-alkyl-N-heteroaralkylamino, cycloalkylalkoxy, cycloalkylalkylthio, N-alkyl-N-cycloalkylalkylamino, azido, arylcarbonylalkoxy, arylcarbonylthio, alkoxycarbonylalkoxy, alkylaminocarbonylalkoxy, alkoxycarbonylalkylthio, alkylaminocarbonylalkylthio, arylcarbonylalkylamino, alkoxycarbonylalkylamino, alkenylthio, alkenylamino, N-alkyl-N-alkenylamino, arylalkenyloxy and alkenyloxy;

wherein $R^2$ is selected from hydrido, hydroxyalkyl, haloalkyl, aminoalkyl, alkoxyalkyl, aralkoxyalkyl, alkylthioalkyl, aralkylthioalkyl, alkylaminoalkyl, aryloxyalkyl, arylthioalkyl, alkylcarbonyloxyalkyl, aminocarbonyl and alkylcarbonylaminoalkyl; and wherein $R^3$ and $R^4$ are independently selected from aryl and heteroaryl, wherein $R^3$ and $R^4$ are optionally substituted at a substitutable position with one or more radicals independently selected from hydrido, alkyl, cyano, carboxyl, alkoxycarbonyl, haloalkyl, hydroxyl, hydroxyalkyl, haloalkoxy, amino, alkylamino, arylamino, nitro, alkoxyalkyl, alkylsulfinyl, halo, alkylsulfonyl, aminosulfonyl, haloalkylsulfonyl, alkoxy and alkylthio;

provided one of $R^3$ and $R^4$ is phenyl substituted with alkylsulfonyl, aminosulfonyl, or haloalkylsulfonyl;

or a pharmaceutically-acceptable salt thereof.

2. Compound of claim 1 wherein $R^1$ is selected from hydrido, halo, $C_1$–$C_{10}$-alkyl, $C_1$–$C_6$-haloalkyl, $C_1$–$C_6$-alkoxy, $C_1$–$C_6$-haloalkoxy, aryl selected from phenyl, naphthyl and biphenyl, $C_1$–$C_6$-alkylthio, $C_1$–$C_6$-alkylamino, $C_1$–$C_6$-di-alkylamino, $C_1$–$C_6$-aralkoxy, $C_1$–$C_6$-aralkylthio, $C_1$–$C_6$-aralkylamino, $C_1$–$C_{10}$—N-alkyl-N-aralkylamino, $C_1$–$C_6$-heteroaralkoxy, $C_1$–$C_6$-heteroaralkylthio, $C_1$–$C_6$-heteroaralkylamino, $C_1$–$C_{10}$—N-alkyl-N-heteroaralkylamino, $C_3$–$C_8$-cycloalkylalkoxy, $C_3$–$C_6$-cycloalkylalkylthio, $C_1$–$C_{10}$—N-alkyl-N-cycloalkylalkylamino, azido, $C_1$–$C_6$-arylcarbonylalkoxy, phenylcarbonylthio, $C_1$–$C_6$-alkoxycarbonylalkoxy, $C_1$–$C_6$-alkylaminocarbonylalkoxy, $C_1$–$C_6$-alkoxycarbonylalkylthio, $C_1$–$C_6$-alkylaminocarbonylalkylthio, $C_1$–$C_6$-arylcarbonylalkylamino, $C_1$–$C_6$-alkoxycarbonylalkylamino, $C_2$–$C_6$-alkenylthio, $C_2$–$C_6$-alkenylamino, $C_1$–$C_{10}$—N-alkyl-N-alkenylamino, $C_2$–$C_6$-arylalkenyloxy and $C_2$–$C_6$-alkenyloxy; wherein $R^2$ is selected from hydrido, $C_1$–$C_6$-hydroxyalkyl, $C_1$–$C_6$-haloalkyl, $C_1$–$C_6$-aminoalkyl, $C_1$–$C_6$-alkoxyalkyl, $C_1$–$C_6$-aralkoxyalkyl, $C_1$–$C_6$-alkylthioalkyl, $C_1$–$C_6$-aralkylthioalkyl, $C_1$–$C_6$-alkylaminoalkyl, $C_1$–$C_{10}$-aryloxyalkyl, $C_1$–$C_6$-arylthioalkyl, $C_1$–$C_{10}$-alkylcarbonyloxyalkyl, aminocarbonyl and $C_1$–$C_{10}$-alkylcarbonylaminoalkyl; and wherein $R^3$ and $R^4$ are independently selected from phenyl, naphthyl, biphenyl and five to ten membered heteroaryl, wherein $R^3$ and $R^4$ are optionally substituted at a substitutable position with one or more radicals independently selected from hydrido, $C_1$–$C_6$-alkylsulfinyl, $C_1$–$C_{10}$-alkyl, cyano, carboxyl, $C_1$–$C_6$-alkoxycarbonyl, $C_1$–$C_6$-haloalkyl, hydroxyl, $C_1$–$C_6$-hydroxyalkyl, $C_1$–$C_6$-haloalkoxy, amino, $C_1$–$C_6$-alkylamino, arylamino, $C_1$–$C_6$-alkoxyalkyl, nitro, halo, $C_1$–$C_6$-alkylsulfonyl, aminosulfonyl, $C_1$–$C_6$-alkoxy and $C_1$–$C_6$-alkylthio; or a pharmaceutically-acceptable salt thereof.

3. Compound of claim 2 wherein $R^1$ is selected from hydrido, halo, $C_1$–$C_6$-alkoxy, $C_1$–$C_6$-haloalkoxy, $C_1$–$C_{10}$-alkyl, aryl selected from phenyl, naphthyl and biphenyl, $C_1$–$C_6$-alkylthio, $C_1$–$C_6$—N-alkylamino, $C_1$–$C_6$-dialkylamino, $C_1$–$C_6$-aralkoxy, $C_1$–$C_6$-aralkylthio, $C_1$–$C_6$-aralkylamino, $C_1$–$C_{10}$—N-alkyl-N-aralkylamino, $C_3$–$C_6$-cycloalkylalkoxy, $C_3$–$C_6$-cycloalkylalkylthio, $C_1$–$C_{10}$—N-alkyl-N-cycloalkylalkylamino, azido, $C_2$–$C_6$-alkenylthio, and $C_2$–$C_6$-alkenyloxy; wherein $R^2$ is selected from hydrido, $C_1$–$C_6$-hydroxyalkyl, $C_1$–$C_6$-haloalkyl, $C_1$–$C_6$-aminoalkyl, $C_1$–$C_{10}$-alkylaminoalkyl, $C_1$–$C_{10}$-alkylcarbonyloxyalkyl, aminocarbonyl and $C_1$–$C_{10}$-alkylcarbonylaminoalkyl; and wherein $R^3$ and $R^4$ are independently selected from phenyl, naphthyl, biphenyl, and five or six membered heteroaryl, wherein $R^3$ and $R^4$ are optionally substituted at a substitutable position with one or more radicals independently selected from hydrido, $C_1$–$C_6$-alkylsulfinyl, $C_1$–$C_{10}$-alkyl, cyano, carboxyl, $C_1$–$C_6$-alkoxycarbonyl, $C_1$–$C_6$-haloalkyl, hydroxyl, $C_1$–$C_6$-hydroxyalkyl, $C_1$–$C_6$-haloalkoxy, amino, $C_1$–$C_6$-alkylamino, arylamino, nitro, halo, $C_1$–$C_6$-alkylsulfonyl, aminosulfonyl, $C_1$–$C_6$-alkoxy and $C_1$–$C_6$-alkylthio; or a pharmaceutically-acceptable salt thereof.

4. Compound of claim 3 wherein $R^1$ is selected from hydrido, halo, $C_1$–$C_{10}$-alkyl, $C_1$–$C_6$-alkoxy, $C_1$–$C_6$-haloalkoxy, phenyl, naphthyl, biphenyl, $C_1$–$C_6$-alkylthio, $C_1$–$C_6$—N-alkylamino, $C_1$–$C_6$-dialkylamino, $C_1$–$C_6$-aralkoxy, $C_1$–$C_6$-aralkylthio, azido and $C_2$–$C_6$-alkenyloxy; wherein $R^2$ is selected from hydrido, $C_1$–$C_6$-hydroxyalkyl, $C_1$–$C_6$-haloalkyl, $C_1$–$C_6$-aminoalkyl, $C_1$–$C_{10}$-alkylaminoalkyl, $C_1$–$C_{10}$-alkylcarbonyloxyalkyl, aminocarbonyl and $C_1$–$C_{10}$-alkylcarbonylaminoalkyl; and wherein $R^3$ and $R^4$ are independently selected from phenyl, thienyl and pyridyl, wherein $R^3$ and $R^4$ are optionally substituted at a substitutable position with one or more radicals independently selected from hydrido, $C_1$–$C_{10}$-alkyl, $C_1$–$C_6$-haloalkyl, $C_1$–$C_6$-haloalkoxy, amino, $C_1$–C6-alkylamino, halo, $C_1$–$C_6$-alkylsulfonyl, aminosulfonyl, $C_1$–$C_6$-alkoxy and $C_1$–$C_6$-alkylthio; or a pharmaceutically-acceptable salt thereof.

5. Compound of claim 4 wherein $R^1$ is selected from hydrido, fluoro, chloro, bromo, methyl, methoxy, ethoxy, propoxy, n-butoxy, pentoxy, hexyloxy, trifluoromethoxy, 4,4,4-trifluorobutoxy, 3,3,3-trifluoropropoxy, phenyl, naphthyl, biphenyl, methylthio, ethylthio, butylthio, hexylthio, methylamino, ethylamino, dimethylamino, butylamino, benzyloxy, phenylethoxy, 4-chlorophenoxy, naphthylmethoxy, benzylthio, phenylethylthio, naphthylmethylthio, azido, hydroxyloxy, and alkenyloxy; wherein $R^2$ is selected from hydrido, hydroxymethyl, 1-methylmethanol, trifluoromethyl, difluoromethyl, fluoromethyl, aminomethyl, N,N-dimethylaminomethyl, N-methylaminomethyl, methylcarbonyloxymethyl, propylcarbonyloxymethyl, propylcarbonyloxyethyl, tert-butylcarbonyloxymethyl, aminocarbonyl and methylcarbonylaminomethyl; and wherein $R^3$ and $R^4$ are independently selected from phenyl, 2-pyridyl, 3-pyridyl and 4-pyridyl, wherein $R^3$ and $R^4$ are optionally substituted at a substitutable position with one or more radicals independently selected from hydrido, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, centafluoroethyl, heptafluoropropyl, fluoromethyl, difluoroethyl, difluoropropyl, dichloroethyl, dichloropropyl, trifluoromethoxy, amino, N-methylamino, N,N-dimethylamino, N-ethylamino, N,N-dipropylamino, N-butylamino, N-methyl-N-ethylamino, fluoro, chloro, bromo, methylsulfonyl, aminosulfonyl, methoxy, methylenedioxy, ethoxy, propoxy, n-butoxy, ethylthio, butylthio, hexylthio and methylthio; or a pharmaceutically-acceptable salt thereof.

6. Compound of claim 2 selected from compounds, and their pharmaceutically acceptable salts, of the group consisting of 2-butoxy-6-(4-fluorophenyl)-N,N-dimethyl-5-[4-5 (methylsulfonyl)phenyl]pyridine-3-methanamine;

2-butoxy-6-(4-fluorophenyl)-5-[4-(methylsulfonyl) phenyl] pyridine-3-methanol, acetate;

[2-butoxy-6-(4-fluorophenyl)-5-[4-(methylsulfonyl) phenyl]pyridin-3-yl]methylbutanoate;

[2-butoxy-6-(4-fluorophenyl) -5-[4-(methylsulfonyl) phenyl]pyridin-3-yl]methyl-2,2-propanoate;

2-butoxy-6-(4-fluorophenyl)-N-methyl-5-[4-(methylsulfonyl)phenyl]pyridine-3-methanamine;

(+/−) 2-butoxy-6-(4-fluorophenyl)-α-methyl-5-[4-(methylsulfonyl)phenyl]pyridine-3-methanol;

(+/−) 1-[2-butoxy-6-(4-fluorophenyl)-5-[4-(methylsulfonyl) phenyl]pyridin-3-yl]ethylbutanoate;

5-[4-aminosulfonyl)phenyl]-2-butoxy-6-(4-fluoro-phenyl)-N,N-dimethyl-pyridine-3-methanamine;

5-[4-(aminosulfonyl)phenyl]-2-butoxy-6-(4-fluorophenyl)-pyridine-3-methanol, acetate;

[5-[4-(aminosulfonyl)phenyl]-2-butoxy-6-(4-fluorophenyl)-pyridin-3-yl]methylbutanoate;

[5-[4-(aminosulfonyl)phenyl]-2-butoxy-6-(4-fluorophenyl)-pyridin-3-yl]methyl-2,2-propanoate;

5-[4-(aminosulfonyl)phenyl]-2-butoxy-6-(4-fluorophenyl)-N-methyl-pyridine-3-methanamine;

(+/−) 5-[4-(aminosulfonyl)phenyl]-2-butoxy-6-(4-fluorophenyl)-α-methyl-pyridine-3-methanol;

(+/−) 1-[5-[4-(aminosulfonyl)phenyl]-2-butoxy-6-(4-fluorophenyl)-pyridin-3-yl]ethylbutanoate;

2-butoxy-6-(4-methylphenyl)-5-[4-(methylsulfonyl) phenyl]pyridine-3-methanol;

2-butoxy-6-(3-methylphenyl)-5-[4-(methylsulfonyl) phenyl]pyridine-3-methanol;

2-butoxy-6-(3-methoxyphenyl)-5-[4-(methylsulfonyl) phenyl]pyridine-3-methanol;

2-butoxy-5-[4-(methylsulfonyl)phenyl]-6-(4-methylthiophenyl)pyridine-3-methanol;

2-butoxy-5-[4-(methylsulfonyl)phenyl]-6-(3-methylthiophenyl)pyridine-3-methanol;

2-butoxy-6-(3-chloro-4-methoxyphenyl)-5-[4 (methylsulfonyl)phenyl]pyridine-3-methanol;

2-butoxy-6-(3-fluoro-4-methoxyphenyl)-5-[4-(methylsulfonyl)phenyl]pyridine-3-methanol;

5-[4-(aminosulfonyl)phenyl]-2-butoxy-6-(4-methylphenyl) pyridine-3-methanol;

5-[4-(aminosulfonyl)phenyl]-2-butoxy-6-(3-methylphenyl) pyridine-3-methanol;

5-[4-(aminosulfonyl)phenyl]-2-butoxy-6-(3-methoxyphenyl)pyridine-3-methanol;

5-[4-(aminosulfonyl)phenyl]-2-butoxy-6-(4-55 methylthiophenyl)pyridine-3-methanol;

5-[4-(aminosulfonyl)phenyl]-2-butoxy-6-(3 methylthiophenyl)pyridine-3-methanol;
5-[4-(aminosulfonyl)phenyl]-2-butoxy-6-(3-chloro-4-methoxyphenyl)pyridine-3-methanol
5-[4-(aminosulfonyl)phenyl]-2-butoxy-6-(3-fluoro-4-methoxyphenyl)pyridine-3-methanol;
2-chloro-6-(4-fluorophenyl)-5-[4-(methylsulfonyl) phenyl] pyridine;
2-methylthio-6-[4-(methylthio)phenyl]-5-[4-(methylsulfonyl)phenyl]pyridine;
2-azido-6-(4-fluorophenyl)-5-[4-(methylsulfonyl) phenyl] pyridine; and
2-chloro-6-(4-fluorophenyl)-5-(4-(methylsulfonyl)phenyl)-3-pyridinecarboxamide.

7. A compound according to claim 1 having the Formula II

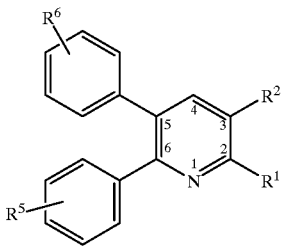

(II)

wherein $R^1$ is selected from hydrido, halo, alkoxy, haloalkoxy, aryl, alkylthio, alkylamino, aralkoxy, azido and alkenyloxy;
wherein $R^2$ is selected from hydrido, hydroxyalkyl, haloalkyl, aminoalkyl, alkylaminoalkyl, alkylcarbonyloxyalkyl, aminocarbonyl and alkylcarbonylaminoalkyl; and
wherein $R^5$ and $R^6$ are one or more radicals independently selected from halo, alkylsulfonyl, aminosulfonyl, alkoxy and alkylthio;
provided one of $R^5$ and $R^6$ is substituted with alkylsulfonyl, aminosulfonyl, or haloalkylsulfonyl;
or a pharmaceutically-acceptable salt thereof.

8. Compound of claim 7 wherein $R^1$ is selected from hydrido, halo, $C_1$–$C_6$-alkoxy, $C_1$–$C_6$-haloalkoxy, aryl selected from phenyl, naphthyl and biphenyl, $C_1$–$C_6$-alkylthio, $C_1$–$C_6$-alkylamino, $C_1$–$C_6$-aralkoxy, azido and $C_2$–$C_6$-alkenyloxy; wherein $R^2$ is selected from hydrido, $C_1$–$C_6$-hydroxyalkyl, $C_1$–$C_6$-haloalkyl, $C_1$–$C_6$-aminoalkyl, $C_1$–$C_{10}$-alkylcarbonyloxyalkyl, aminocarbonyl and $C_1$–$C_{10}$-alkylcarbonylaminoalkyl; and wherein $R^5$ and $R^6$ are one or more radicals independently selected from halo, $C_1$–$C_6$-alkylsulfonyl, aminosulfonyl, $C_1$–$C_6$-alkoxy and $C_1$–$C_6$-alkylthio; or a pharmaceutically-accceptable salt thereof.

9. A pharmaceutical composition comprising a therapeutically-effective amount of a compound, said compound selected from a family of compounds of claim 1; or a pharmaceutically-acceptable salt thereof.

10. A pharmaceutical composition comprising a therapeutically-effective amount of a compound, said compound selected from a family of compounds of claim 2; or a pharmaceutically-acceptable salt thereof.

11. A pharmaceutical composition comprising a therapeutically-effective amount of a compound, said compound selected from a family of compounds of claim 3; or a pharmaceutically-acceptable salt thereof.

12. A pharmaceutical composition comprising a therapeutically-effective amount of a compound, said compound selected from a family of compounds of claim 4; or a pharmaceutically-acceptable salt thereof.

13. A pharmaceutical composition comprising a therapeutically-effective amount of a compound, said compound selected from a family of compounds of claim 5; or a pharmaceutically-acceptable salt thereof.

14. A pharmaceutical composition comprising a therapeutically-effective amount of a compound, said compound selected from a family of compounds of claim 6; or a pharmaceutically-acceptable salt thereof.

15. A pharmaceutical composition comprising a therapeutically-effective amount of a compound, said compound selected from a family of compounds of claim 7; or a pharmaceutically-acceptable salt thereof.

16. A pharmaceutical composition comprising a therapeutically-effective amount of a compound, said compound selected from a family of compounds of claim 8; or a pharmaceutically-acceptable salt thereof.

17. A method-of treating inflammation or an inflammation-associated disorder in a subject, said method comprising treating the subject having or susceptible to said disorder with a therapeutically-effective amount of a compound of claim 1; or a pharmaceutically-acceptable salt thereof.

18. A method of treating inflammation or an inflammation-associated disorder in a subject, said method comprising treating the subject having or susceptible to said disorder with a therapeutically-effective amount of a compound of claim 2; or a pharmaceutically-acceptable salt thereof.

19. A method of treating inflammation or an inflammation-associated disorder in a subject, said method comprising treating the subject having or susceptible to said disorder with a therapeutically-effective amount of a compound of claim 3; or a pharmaceutically-acceptable salt thereof.

20. A method of treating inflammation or an inflammation-associated disorder in a subject, said method comprising treating the subject having or susceptible to said disorder with a therapeutically-effective amount of a compound of claim 4; or a pharmaceutically-acceptable salt thereof.

21. A method of treating inflammation or an inflammation-associated disorder in a subject, said method comprising treating the subject having or susceptible to said disorder with a therapeutically-effective amount of a compound of claim 5; or a pharmaceutically-acceptable salt thereof.

22. A method of treating inflammation or an inflammation-associated disorder in a subject, said method comprising treating the subject having or susceptible to said disorder with a therapeutically-effective amount of a compound of claim 6; or a pharmaceutically-acceptable salt thereof.

23. A method of treating inflammation or an inflammation-associated disorder in a subject, said method comprising treating the subject having or susceptible to said disorder with a therapeutically-effective amount of a compound of claim 7; or a pharmaceutically-acceptable salt thereof.

24. A method of treating inflammation or an inflammation-associated disorder in a subject, said method comprising treating the subject having or susceptible to said disorder with a therapeutically-effective amount of a compound of claim 8; or a pharmaceutically-acceptable salt thereof.

25. The method of claim 17 for use in treatment of inflammation.

26. The method of claim 17 for use in treatment of an inflammation-associated disorder.

27. The method of claim 26 wherein the inflammation-associated disorder is arthritis.

28. The method of claim 26 wherein the inflammation-associated disorder is pain.

29. The method of claim 26 wherein the inflammation-associated disorder is fever.

* * * * *